(12) United States Patent
Abubshait et al.

(10) Patent No.: US 12,281,086 B2
(45) Date of Patent: Apr. 22, 2025

(54) 2-AMINOTHIAZOLES DERIVATIVES AND METHOD OF PREPARATION THEREOF USING SUPER-PARAMAGNETIC IRON OXIDE NANOPARTICLES (SPIONs)

(71) Applicant: Imam Abdulrahman Bin Faisal University, Dammam (SA)

(72) Inventors: Samar A. Abubshait, Dammam (SA);
Haya A. Abubshait, Dammam (SA);
Sara Nabil Shaban, Cairo (EG); Asma Mohmmad Elsharif, Dammam (SA);
Hamad M. Alkahtani, Riyadh (SA);
Fadilah Sfouq Aleanizy, Riyadh (SA);
M. Nasiruzzaman Shaikh, Dhahran (SA)

(73) Assignee: Imam Abdulrahman Bin Faisal Universty, Dammam (SA)

( * ) Notice: Subject to any disclaimer, the term of this patent is extended or adjusted under 35 U.S.C. 154(b) by 82 days.

(21) Appl. No.: 18/181,965

(22) Filed: Mar. 10, 2023

(65) Prior Publication Data
US 2024/0300909 A1    Sep. 12, 2024

(51) Int. Cl.
*C07D 277/50*    (2006.01)
*A61P 31/04*    (2006.01)
*B01J 23/745*    (2006.01)
*C07D 417/12*    (2006.01)

(52) U.S. Cl.
CPC ............ *C07D 277/50* (2013.01); *A61P 31/04* (2018.01); *B01J 23/745* (2013.01); *C07D 417/12* (2013.01)

(58) Field of Classification Search
CPC ..... C07D 277/50; C07D 417/12; A61P 31/04; B01J 23/745
See application file for complete search history.

(56) References Cited

U.S. PATENT DOCUMENTS 9,775,919 B2   10/2017   Pattayil et al.
9,844,679 B2   12/2017   Nayfach-Battilana
9,950,082 B2    4/2018   Doschak et al.
10,858,327 B2  12/2020   Shaikh et al.

OTHER PUBLICATIONS

Mhaibes, R., & Al-Tamimi, E. (2021). Synthesis of new heterocyclic containing azo group from 2-N-chloro acetamido creatinine and studying their biological activity. Eurasian Chemical Communications, 3(6), 401-405. doi: 10.22034/ecc.2021.281946.117 (Year: 2021).*

(Continued)

*Primary Examiner* — Joseph K McKane
*Assistant Examiner* — Anna Grace Kuckla
(74) *Attorney, Agent, or Firm* — Oblon, McClelland, Maier & Neustadt, L.L.P.

(57) ABSTRACT

A method of making a pyrazole compound includes mixing a diazonium salt with a reactant in the presence of a solvent, thereby coupling a diazo group of the diazonium salt to an α-carbon atom of the reactant to form a reaction intermediate having a formula of (I) or (II); mixing the reaction intermediate and hydrazine in the presence of a superparamagnetic iron oxide nanoparticles catalyst thereby cyclizing the hydrazine with an ester group of the reaction intermediate to form the pyrazole compound having a formula of (III) or (IV).

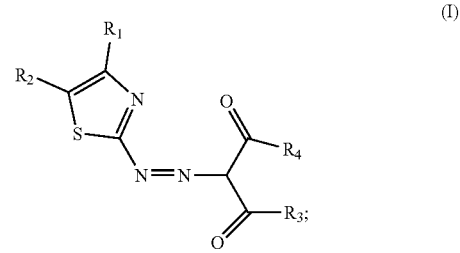

(I)

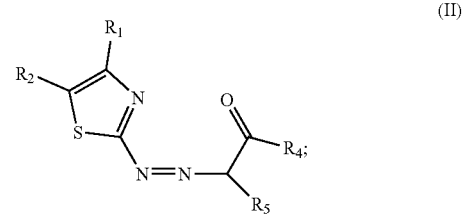

(II)

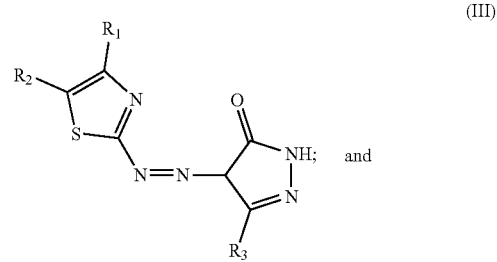

(III) and

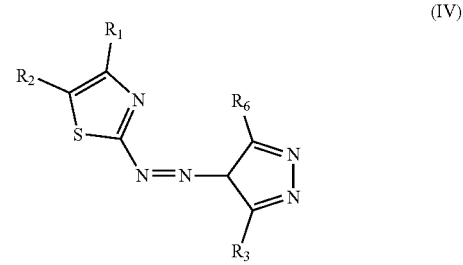

(IV)

12 Claims, 11 Drawing Sheets

(56) References Cited

OTHER PUBLICATIONS

Synthesis of 2-aminothiazoles from methylcarbonyl compounds using a Fe304 nanoparticle-N-halo reagent catalytic system Sadeghi, Masoud, Safari, Javad, Zarnegar, Zohre, 2016, 64749, 64755, RSC Advances, RSC Adv., 6, 69, The Royal Society of Chemistry (Year: 2016).*

Shafeeulla M, Krishnamurthy G, Bhojynaik HS, T M. Synthesis, Cytotoxicity and Molecular Docking Study of Complexes Containing Thiazole Moiety. JOTCSA. 2017;4(3):787-810. (Year: 2017).*

Mohammed Albratty, et al., "Synthesis and antitumor activity of some novel thiophene, pyrimidine, coumarin, pyrazole and pyridine derivatives", Acta Pharmaceutica, vol. 67, Edition 1, Mar. 2017, pp. 15-33.

H. Maleki, et al., "Size-controlled synthesis of superparamagnetic iron oxide nanoparticles and their surface coating by gold for biomedical applications", Journal of Magnetism and Magnetic Materials, vol. 324, Issue 23, Nov. 2012, pp. 3997-4005.

Vitalii Patsula, et al., "Size-dependent magnetic properties of iron oxide nanoparticles", Journal of Physics and Chemistry of Solids, vol. 88, Jan. 2016, pp. 24-30.

\* cited by examiner

50

52 — Mix a diazonium salt with a reactant in the presence of a solvent thereby coupling a diazo group of the diazonium salt to an α-carbon atom of the reactant to form a reaction intermediate having a formula selected from the group consisting of (I) and (II)

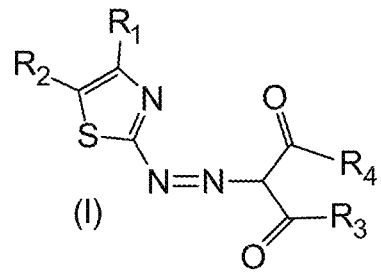
(I)

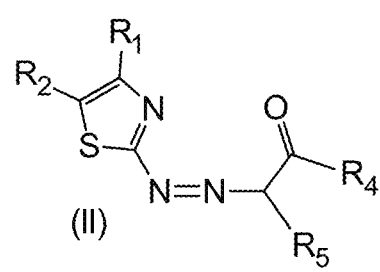
(II)

54 — Mix the reaction intermediate and hydrazine in the presence of a superparamagnetic iron oxide nanoparticles (SPIONs) catalyst thereby cyclizing the hydrazine with an ester group of the reaction intermediate to form the pyrazole compound having a formula selected from the group consisting of (III) and (IV)

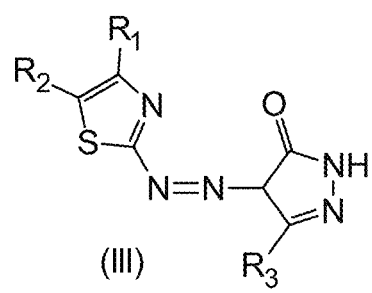
(III)

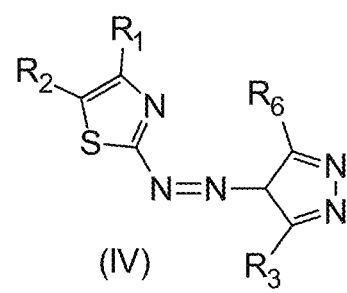
(IV)

FIG. 1A

2-AMINOTHIAZOLES DERIVATIVES AND METHOD OF PREPARATION THEREOF USING SUPER-PARAMAGNETIC IRON OXIDE NANOPARTICLES (SPIONs)

STATEMENT REGARDING PRIOR DISCLOSURE BY THE INVENTORS

Aspects of this technology are described in "SPIONs as a nanomagnetic catalyst for the synthesis and anti-microbial activity of 2-aminothiazoles derivatives," Arabian Journal of Chemistry, Volume 15, Issue 7, 103878, which is incorporated herein by reference in its entirety.

STATEMENT OF ACKNOWLEDGEMENT

This research was supported by the Deanship of Scientific Research at Imam Abdulrhaman Bin Faisal University under the project 2019-132-sci, the Basic and Applied Scientific Research Center at Imam Abdulrhaman Bin Faisal University, and the Pharmaceutical Chemistry and Chemistry Department at King Saud University.

BACKGROUND

Technical Field

The present disclosure is directed to aminothiazole derivatives, particularly, to a method of synthesizing the aminothiazole derivatives using SPIONs nanomagnetic catalysis.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Thiazole is a core structural element that plays an important role in nature and has a wide range of applications in medicinal chemistry [D. Das, P. Sikdar, M. Bairagi, Recent developments of 2-aminothiazoles in medicinal chemistry, Eur. J. Med. Chem., 109 (2016), pp. 89-98; and B. Smith, H. H. Chang, F. Medda, V. Gokhale, J. Dietrich, Synthesis and biological activity of 2-aminothiazoles as novel inhibitors of PGE2 production in cells, Bioorg. Med. Chem. Lett., 22 (2012), pp. 3567-3570]. Thiazole heterocycle is a main structural motif of many natural compounds such as vitamin B1 (thiamine), penicillin, and carboxylase [Y. P. Zhu, J. J. Yuan, Q. Zhao, M. Lian, Q. H. Gao, M. C. Liu, Y. Yang, A. X. Wu, $I_2$/CuO-catalyzed tandem cyclization strategy for one-pot synthesis of substituted 2-aminothiozole from easily available aromatic ketones/α, β-unsaturated ketones and thiourea, Tetrahedron, 68 (2012), pp. 173-178]. 2-Aminothiazoles are one of the most important classes of heterocyclic compounds, that contain nitrogen and sulfur present in compounds possessing scaffolds due to medical and pharmaceutical applications, such as antihypertension [W. C. Patt, H. W. Hamilton, M. D. Taylor, M. J. Ryan, D. G. Taylor, C. J. C. Connolly, A. M. Doherty, S. R. Klutchko, I. Sircar, B. A. Steinbaugh, B. L. Batley, C. A. Painchaud, S. T. Rapundalo, B. M. Michniewicz, S. C. Olson, Structure activity relationship of a series of 2-amino-4-thiazole-containing renin inhibitors, J. Med. Chem., 35 (1992), pp. 2562-2527], antibacterial [J. Joseph, G. B. Janaki, K. Nagashri, R. S. Joseyphus, Antimicrobial, Antioxidant, and SOD activities of copper (II) complexes derived from 2-Aminobenzo thiazole derivatives, J. Coordination Chem., 70 (2017), pp. 242-260], anti-inflammation, antiviral [T. K. Venkatachalam, E. A. Sudbeck, C. Mao, F. M. Uckun, Anti-HIV activity of aromatic and heterocyclic thiazolyl thiourea compounds, Bioorg. Med. Chem., 11 (2001), pp. 523-528], antimycobacterial [P. Makam, R. Kankanala, A. Prakash, T. Kannan, 2-(2-Hydrazinyl) thiazole derivatives: design, synthesis, and in vitro antimycobacterial studies, Eur. J. Med. Chem., 69 (2013), pp. 564-576], anticonvulsant [N. Siddiqui, W. Ahsan, Triazole incorporated thiazoles as a new class of anticonvulsants: design, synthesis, and in vivo screening, Eur. J. Med. Chem., 45 (2010), pp. 1536-1543], antileishmanial [D. Bhuniya, R. Mukhhavilli, R. Shivhare, D. Launay, R. T. Dere, A. Deshpandey, A. Verma, P. Vishwakarma, M. Moger, A. Pradhan, H. Pati, V. S. Gopinath, S. Gupta, S. Puri, D. Martin, Aminothiazoles: Hit to lead development to identify antileishmanial agents, Eur. J. Med. Chem., 102 (2015), pp. 582-593], HIV infections [F. W. Bell, A. S. Cantrell, M. Hogberg, S. R. Jaskunas, N. G. Johansson, C. L. Jordan, M. D. Kinnick, P. Lind, J. M. Morin, R. NorBen, B. Oberg, J. A. Palkowitz, C. A. Parrish, P. Pranc, C. Sahlberg, R. J. Ternansky, R. T. Vasileff, L. Vrang, S. J. West, H. Zhang, X. X. Zhou, Phenethylthiazolethiouea (PETT) compounds, a new class of HIV-1 reverse transciptase inhibitors. 1. Synthesis and basic structure activity relationship studies of PETT analogs, J. Med. Chem., 38 (1995), pp. 4929-4936], antitumor [M. F. Elsadek, B. M. Ahmed, M. F. Farahat, An overview on synthetic 2-aminothiazole-based compounds associated with four biological activities, Molecules, 26 (2021), p. 1449], antidiabetic [J. Joseph, G. B. Janaki, K. Nagashri, R. S. Joseyphus, Antimicrobial, Antioxidant, and SOD activities of copper (II) complexes derived from 2-Aminobenzo thiazole derivatives, J. Coordination Chem., 70 (2017), pp. 242-260], and antioxidative [O. Uchikawa, K. Fukatsu, M. Suno, T. Aono, T. Doi, In vivo biological activity of antioxidative aminothiazole derivatives, Chem. Pharm. Bull., 44 (1996), pp. 2070-2077]. Therefore, increasing attention has been paid to the synthesis of heterocycles compounds. The development of an environmentally benign and efficient procedure for the synthesis of 2-aminothiazoles derivatives remains a great challenge.

In view of the forgoing, one objective of the present disclosure is to provide a procedure for the synthesis of 2-aminothiazole derivatives, for example reaction in the presence of a superparamagnetic iron oxide nanoparticle (SPIONs) catalyst. A further objective of the present disclosure is to describe a method of making the superparamagnetic iron oxide nanoparticles (SPIONs) catalyst.

SUMMARY

In an exemplary embodiment, a method of making a pyrazole compound is described. The method includes mixing a diazonium salt with a reactant in the presence of a solvent thereby coupling a diazo group of the diazonium salt to an a-carbon atom of the reactant to form a reaction intermediate having a formula selected from the group consisting of (I) and (II). The method also includes mixing the reaction intermediate and hydrazine in the presence of a superparamagnetic iron oxide nanoparticles (SPIONs) catalyst thereby cyclizing the hydrazine with an ester group of the reaction intermediate to form the pyrazole compound having a formula selected from the group consisting of (III), and (IV).

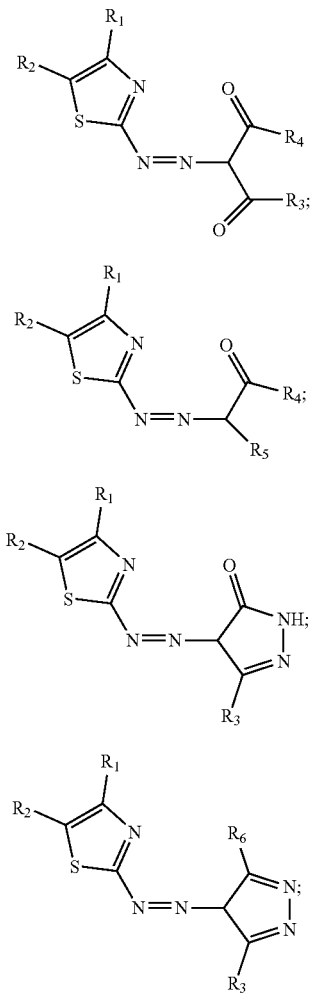

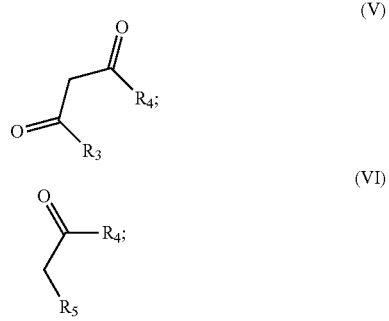

where $R_1$, $R_2$, $R_3$, $R_4$, $R_5$, and $R_6$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group.

In some embodiments, the aminothiazole compound is present in the first mixture at a concentration of 0.1 to 0.6 molars (M). In some embodiments, a molar ratio of the aminothiazole compound to the nitrite salt is in a range of 1:1 to 1:10.

In some embodiments, the aminothiazole compound is 2-aminothiazole, and where $R_1$ and $R_2$ are each independently a hydrogen atom.

In some embodiments, the nitrite salt is at least one selected from the group consisting of sodium nitrite, potassium nitrite, and lithium nitrite.

In some embodiments, the diazonium salt is 2-(chlorodiazenyl)thiazole, where $R_1$ and $R_2$ are each independently a hydrogen atom, and X is chloride.

In some embodiments, the reactant has a formula selected from the group consisting of (V) and (VI).

and where $R_3$, $R_4$, and $R_5$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group.

In some embodiments, the reactant is at least one selected from the group consisting of methyl acetoacetate, ethyl acetoacetate, ethyl cyanoacetate, malononitrile and acetylacetone.

In some embodiments, a molar ratio of the diazonium salt to the reactant is in a range of 1:1 to 1:3.

In some embodiments, the solvent is at least one selected from the group consisting of toluene, benzene, dichloromethane, dichloroethane, chloroform, methanol, ethanol, propanol, butanol, dimethylformamide, dimethylacetamide, dimethylsulfoxide, tetrahydrofuran, and acetonitrile.

In some embodiments, $R_1$ and $R_2$ are each independently a hydrogen atom, where $R_3$, $R_4$, and $R_5$ are each independently selected from the group consisting of a methyl group, an ethoxy group, a cyano group, and where the reaction intermediate is at least one selected from the group consisting of ethyl 3-oxo-2-(thiazol-2yldiazenyl)butanoate, ethyl 2-cyano-2-(thiazol-2-yldiazenyl)acetate, and 3-(thiazol-2-yl-hydrazono)-pentane-2,4-dione.

In some embodiments, a molar ratio of the SPIONs catalyst having a formula $Fe_3O_4$ to the reaction intermediate is in a range of 1:200 to 1:10.

In some embodiments, $R_1$ and $R_2$ are each independently a hydrogen atom, where $R_3$ and $R_6$ are each independently selected from the group consisting of a methyl group, and an amine group. The pyrazole compound is at least one selected from the group consisting of 3-methyl-4-(thiazol-2-yldiazenyl)-1H-pyrazol-5(4H)-one, 3-amino-4-(thiazol-2-yldiazenyl)-1H-pyrazol-5(4H)-one, and (3,5-dimethyl-4H-pyrazol-4-yl)-thiazol-2-yl-diazene.

In some embodiments, the pyrazole compound can inhibit microbial growth of at least one selected from the group consisting of E. coli, P. aeruginosa, B. subtilis, S. aureus, and C. albicans.

In another exemplary embodiment, the method of making a pyrazole compound further includes preparing the diazonium salt. The method of preparing the diazonium salt includes mixing and dissolving an aminothiazole compound having a formula (VII) in an acid solution to form a mixture. The method of preparing the diazonium salt further includes diazotizing the aminothiazole compound by mixing a nitrite salt with the mixture to form the diazonium salt having a formula (VIII).

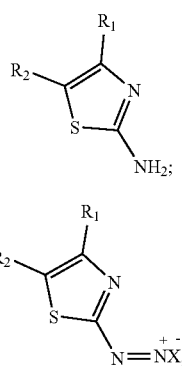

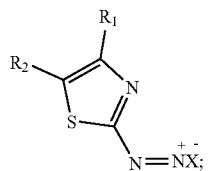

where $R_1$ and $R_2$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group; and where X is a halogen atom.

In some embodiments, the aminothiazole compound is present in the mixture at a concentration of 0.1 to 0.6 molar (M). In some embodiments, a molar ratio of the aminothiazole compound to the nitrite salt is in a range of 1:1 to 1:10.

In some embodiments, the aminothiazole compound is 2-aminothiazole. In some embodiments, the nitrite salt is at least one selected from the group consisting of sodium nitrite, potassium nitrite, and lithium nitrite.

In another exemplary embodiment, a method of making a Schiff base is described. The method includes mixing an aminothiazole compound having a formula (VII), and an aromatic aldehyde in the presence of a superparamagnetic iron oxide nanoparticles (SPIONs) catalyst thereby condensing the aromatic aldehyde with an amine group of the aminothiazole compound to form the Schiff base having a formula (IX).

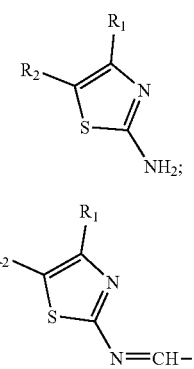

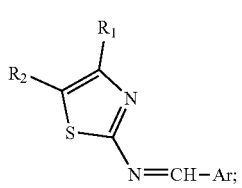

where $R_1$ and $R_2$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group; and where Ar is selected from the group consisting of —$C_6H_5$, p-($C_6H_4$)—Cl, o-($C_6H_4$)—$NO_2$, p-($C_6H_4$)—OH, o-($C_6H_4$)—OH, p-($C_6H_4$)—OMe, o-($C_6H_4$)—OMe, 2,4-($C_6H_3$)—$(OMe)_2$, and 2,3-($C_6H_3$)—$(OMe)2$,2-methylindolyl-4-.

In some embodiments, a molar ratio of the aminothiazole compound to the aromatic aldehyde is in a range of 1:1 to 1:3.

In some embodiments, a molar ratio of the SPIONs catalyst having a formula $Fe_3O_4$ to the aminothiazole compound is in a range of 1:200 to 1:10.

In some embodiments, the aromatic aldehyde is at least one aldehyde selected from the group consisting of benzaldehyde, p-chlorobenzaldehyde, o-nitrobenzaldehyde, p-hydroxybenzaldehyde, salicylladehyde, p-anisaldehyde, o-anisaldehyde, 2,4-dimethoxybenzaldehyde, 2,3-dimethoxybenzaldehyde, and 2-methyl indolyl-3-carboxaldehyde.

In some embodiments, the Schiff base is at least one selected from the group consisting of N-(benzylidene)thiazol-2-amine, N-(4-chlorobenzylidene)thiazol-2-amine, N-(2-nitrobenzylidene)thiazol-2-amine, 4-((thiazol-2-ylimino)methyl)phenol, 2-((thiazol-2-ylimino)methyl)phenol, N-(4-methoxybenzylidene)thiazol-2-amine, N-(2-methoxybenzylidene)thiazol-2-amine, N-(2,4-dimethoxybenzylidene)-thiazol-2-yl-amine, N-(2,3-dimethoxybenzylidene)thiazol-2-amine, and N-((2-methyl-1H-indol-3-yl)methylene)thiazol-2-amine.

In some embodiments, the Schiff base can inhibit microbial growth of at least one selected from the group consisting of *E. coli, P. aeruginosa, B. subtilis, S. aureus*, and *C. albicans*.

In some embodiments, the method further includes preparing the superparamagnetic iron oxide nanoparticles (SPIONs) catalyst by mixing an iron (II) salt and an iron (III) salt in water to form a mixture under an inert atmosphere. The method of preparing the SPIONs catalyst further involves heating the mixture to a temperature of 80 to 100° C., and mixing with an ammonium hydroxide solution to form a reaction mixture having a pH of 8 to 10. The method of preparing the SPIONs catalyst further involves continuously agitating the reaction mixture to form the SPIONs in the form of a precipitate. Additionally, the method of preparing the SPIONs catalyst involves removing the precipitate from the reaction mixture, washing, and drying to form the SPIONs catalyst. In some embodiments, the SPIONs are in the shape of spherical particles having an average particle size of 2 to 20 nanometers (nm). In some embodiments, a molar ratio of the iron (II) salt to the iron (III) salt in the mixture is 2:1 to 1:4. In some embodiments, the ammonium hydroxide solution has an ammonia concentration of 15 to 30% by mass.

In some embodiments, the iron (II) salt includes iron (II) fluoride, iron (II) chloride, iron (II) bromide, and its hydrate. The iron (III) salt includes iron (III) fluoride, iron (III) chloride, iron (III) bromide, and its hydrate.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 1A is a schematic flow chart of a method of making a pyrazole compound, according to certain embodiments;

DETAILED DESCRIPTION

Figure 1B:
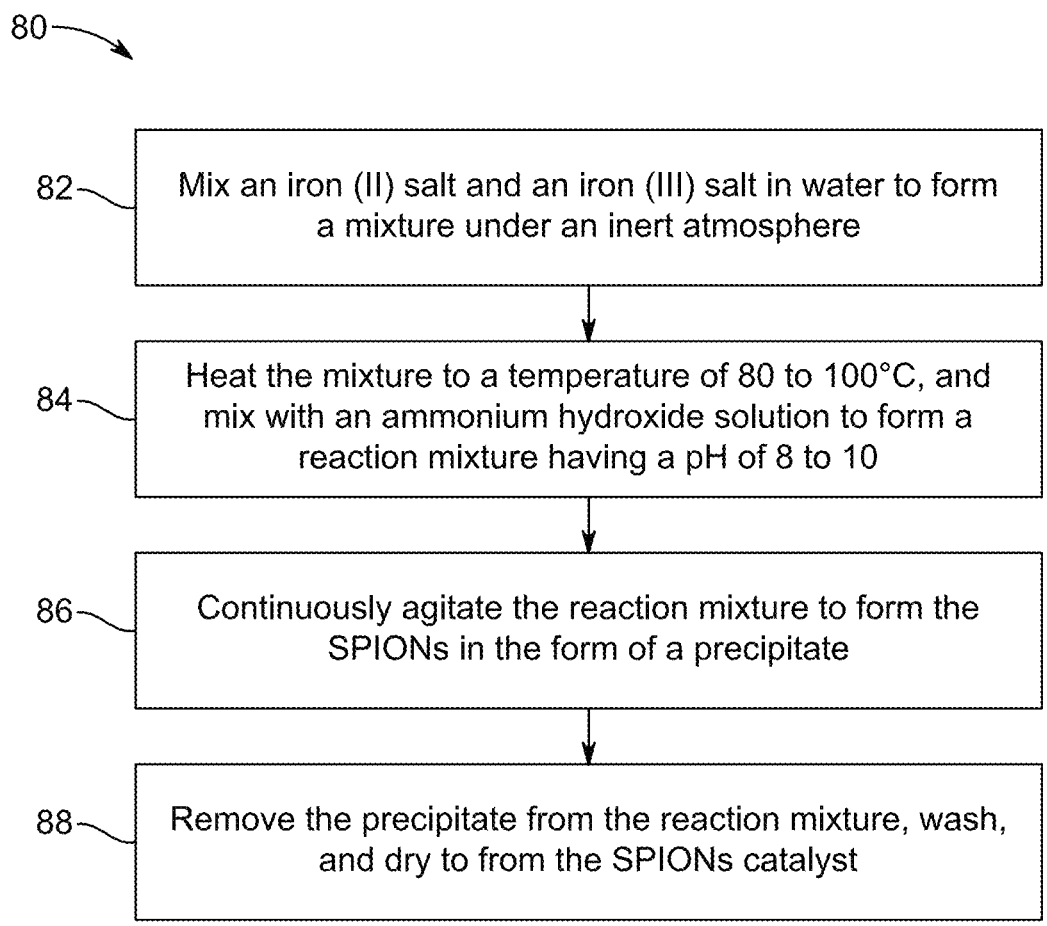
FIG. 1B is a schematic flow chart of a method of preparing a SPIONs catalyst, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

As used herein, the term 'pyrazole compound,' 'pyrazolyl compound,' or 'pyrazolyl derivatives' refers to the organic compound containing the structure of formula $C_3H_3N_2$—. The pyrazole compound is a heterocycle characterized by a 5-membered ring of three carbon atoms and two adjacent nitrogen atoms in ortho-substitution.

As used herein, the term 'diazonium salt' refers to the organic compounds sharing a functional group [R—N$^+$≡N] X$^-$ where R can be an organic group, such as an alkyl or an aryl, and X is an inorganic or organic anion, such as a halide.

Aspects of the present invention are directed towards the synthesis of aminothiazole derivatives using ultrasmall superparamagnetic iron oxide nanoparticles (SPIONs) nano-magnetic catalysis. The SPIONs was prepared by reducing Fe (II) and Fe (III) precursors using aqueous ammonia. The aminothiazole derivatives and the SPIONs were then characterized by chemical analytical techniques such as X-Ray diffraction (XRD), Fourier transform infrared (FTIR), scanning electron microscope (SEM), and Transmission electron microscopy (TEM). 2-aminothiazole derivatives were obtained by coupling 2-aminothiazole diazonium salt with active methylene compounds and cyclization with hydrazine hydrate to afford pyrazolyl derivatives. The one-pot reaction of 2-aminothiazole with an aromatic aldehyde in $Fe_3O_4NPs$ gives Schiff base derivatives. The present reaction includes green and clean conditions, short reaction time, improved yield of products with high purity, easy separation, easy work-up procedure, low cost, and operational simplicity, thereby circumventing the drawbacks of the prior art. Furthermore, the synthesized compounds were evaluated for their anti-microbial activity. In some embodiments, the synthesized compounds have anti-fungal, anti-tubercular, anti-inflammatory properties, anticonvulsant, anticancer, and anti-viral activities.

FIG. 1A illustrates a schematic flow chart of a method 50 of making a pyrazole compound. The order in which the method 50 described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes mixing a diazonium salt with a reactant in the presence of a solvent, thereby coupling a diazo group of the diazonium salt to an α-carbon atom of the reactant to form a reaction intermediate having a formula selected from the group consisting of (III) and (IV).

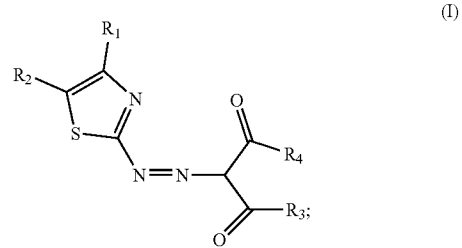

(I)

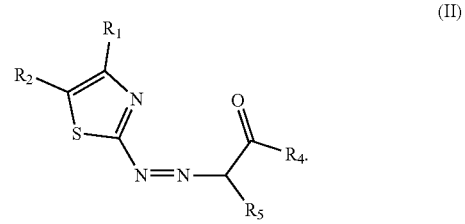

(II)

In some embodiments, $R_1$, $R_2$, $R_3$, and $R_4$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group. In a preferred embodiment, $R_1$ and $R_2$ are each independently a hydrogen atom. In some embodiments, $R_1$ and $R_2$ are each independently a hydrogen atom, where $R_3$, $R_4$, and $R_5$ are each independently selected from the group consisting of a methyl group, an ethoxy group, and a cyano group.

As used herein, the term 'α-carbon atom,' or 'α-carbon' 'alpha-carbon' generally refers to a carbon atom of a molecue that is bonded to a functional group of that same molecule.

In an embodiment, the diazonium salt is 2-(chlorodiazenyl)thiazole. In some embodiments, the reactant has a formula selected from the group consisting of (V) and (VI).

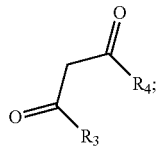

(V)

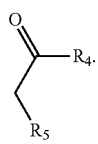

(VI)

In some embodiments, $R_3$, $R_4$, and $R_5$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group. In some embodiments, the reactant is at least one selected from the group consisting of methyl acetoacetate, ethyl acetoacetate, ethyl cyanoacetate, malononitrile and acetylacetone.

In some embodiments, a molar ratio of the diazonium salt to the reactant is in a range of 1:1 to 1:3, more preferably 1:1. Other ranges are also possible. In some embodiments, this reaction is carried in the presence of a solvent. In some further embodiments, the solvent is at least one selected from the group consisting of toluene, benzene, dichloromethane, dichloroethane, chloroform, methanol, ethanol, propanol, butanol, dimethylformamide, dimethylacetamide, dimethylsulfoxide, tetrahydrofuran, and acetonitrile. In the preferred embodiment, the solvent is ethanol. The reaction between the diazonium salt and the reactant causes coupling of the diazo group of the diazonium salt to an α-carbon atom of the reactant to form the reaction intermediate. In some further preferred embodiments, the reaction intermediate is at least one selected from the group consisting of ethyl 3-oxo-2-(thiazol-2yldiazenyl)butanoate, ethyl 2-cyano-2-(thiazol-2-yldiazenyl)acetate, and 3-(thiazol-2-yl-hydrazono)-pentane-2,4-dione.

At step 54, the method 50 includes mixing the reaction intermediate and hydrazine in the presence of a superparamagnetic iron oxide nanoparticles (SPIONs) catalyst, thereby cyclizing the hydrazine with an ester group of the reaction intermediate to form the pyrazole compound having a formula selected from the group consisting of (V), and (VI);

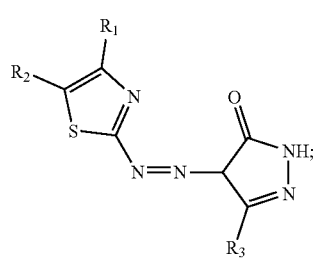

(III)

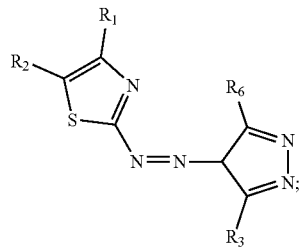

(IV)

In some embodiments, $R_1$, $R_2$, $R_3$, and $R_6$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group. In some embodiments, $R_1$ and $R_2$ are independent hydrogen atoms, where $R_3$ and $R_6$ are each independently selected from the methyl and amine groups.

In some embodiments, a molar ratio of the SPIONs catalyst having a formula $Fe_3O_4$ to the reaction intermediate is in a range of 1:200 to 1:10, more preferably 1:100. In some embodiments, the pyrazole compound is at least one selected from the group consisting of 3-methyl-4-(thiazol-2-yldiazenyl)-1H-pyrazol-5(4H)-one, 3-amino-4-(thiazol-2-yldiazenyl)-1H-pyrazol-5(4H)-one, and (3,5-dimethyl-4H-pyrazol-4-yl)-thiazol-2-yl-diazene. For all the formulae (I-IV), $R_1$, $R_2$, $R_3$, $R_4$, $R_5$, and $R_6$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group.

Figure 6:
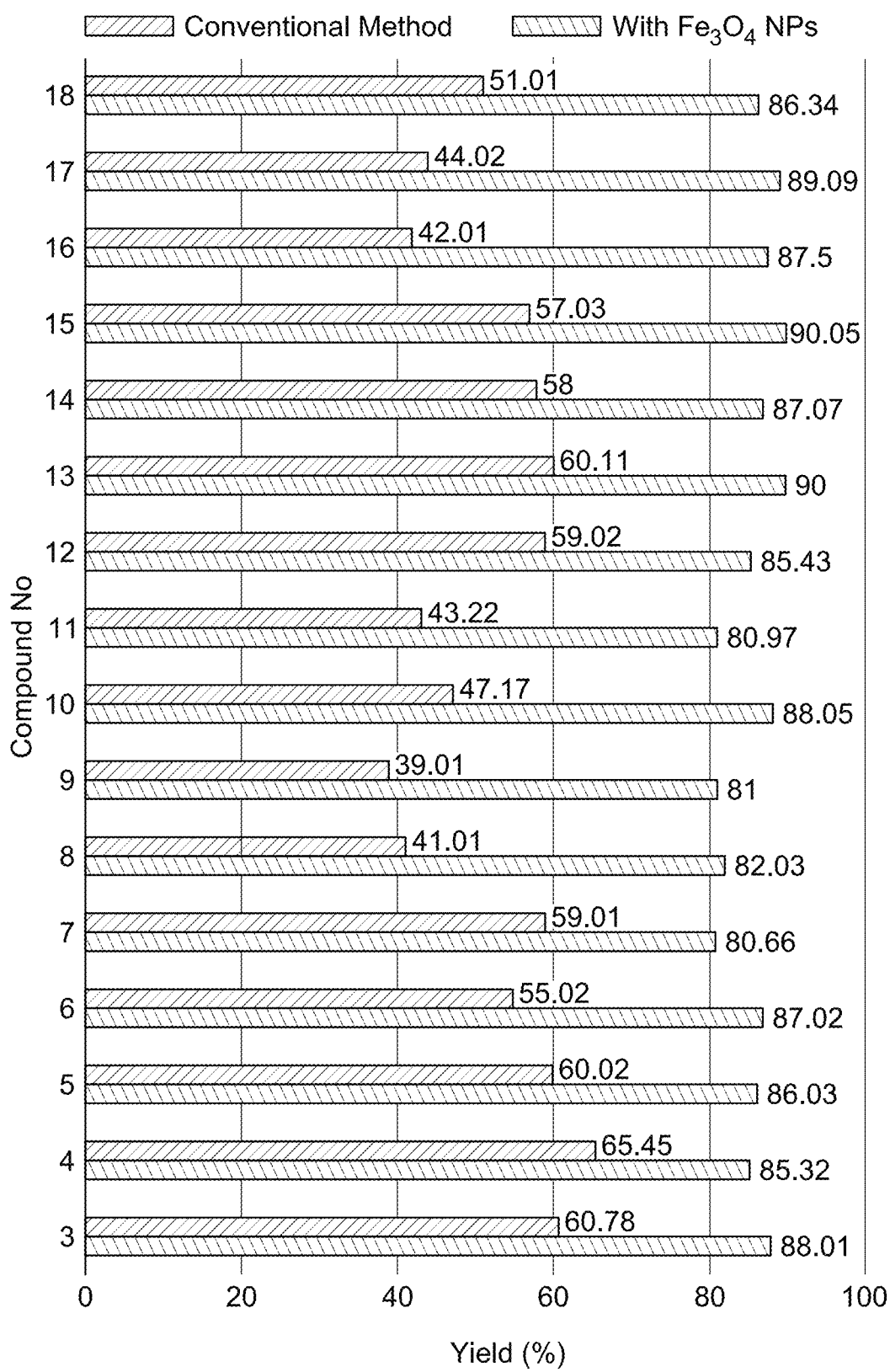
FIG. 6 depicts an effect on yield of products using conventional methods and with the $Fe_3O_4NPs$ catalysis, according to certain embodiments.

Referring to FIG. 6, in some embodiments, the method 50 has a product yield in a range of 70 to 90% based on an initial amount of the aminothiazole compound, more preferably 80 to 88%. In some further embodiments, the method of making 50 has a reaction time in a range of 2 to 40 minutes, more preferably 15 minutes. Other ranges are also possible.

In some embodiments, the compounds of formula (I-VI) can inhibit microbial growth of at least one selected from the group consisting of E. coli, P. aeruginosa, B. subtilis, S. aureus, and C. albicans. In addition, the compounds of formula (I-VI) may also inhibit microbial growth of Campylobacter, Clostridium perfringens, Listeria, Norovirus, Salmonella, Deinococcus radiodurans, Myxococcus xanthus, and Yersinia pestis.

According to another aspect of the present disclosure, the method 50 also includes preparing the diazonium salt. The method of preparing the diazonium salt includes mixing and dissolving an aminothiazole compound having a formula (VII) in an acid solution to form a mixture. The method of preparing the diazonium salt further includes diazotizing the aminothiazole compound by mixing a nitrite salt with the mixture to form the diazonium salt having a formula (VIII).

(VII)

-continued

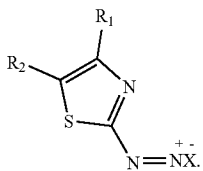
(VIII)

In some embodiments, $R_1$ and $R_2$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group. In some embodiments, X is a halogen atom.

In a preferred embodiment, the compound of formula (VII) is 2-aminothiazole, where $R_1$ and $R_2$ are each independently a hydrogen atom. In some embodiments, the acid solution may include but are not limited to phosphoric acid, sulphuric acid, nitric acid, acetic acid, perchloric acid, picric acid, citric acid, and hydrochloric acid. In the preferred embodiment, the acid solution is hydrochloric acid. In some embodiments, the concentration of the aminothiazole compound present in the first mixture is 0.001 to 1 molars (M), preferably 0.1 to 0.8 M, preferably 0.2 to 0.6 M, or even more preferably 0.3 to 0.4 M. Other ranges are also possible. In a preferred embodiment, the mixing is carried out in an ice bath. In some embodiments, the temperature of the ice bath is in a range of −10 to 5° C. Other ranges are also possible.

The method of preparing the diazonium salt further includes mixing a nitrite salt with the mixture at a temperature of −10 to 5° C. thereby diazotizing the aminothiazole compound to form a diazonium salt having formula (II).

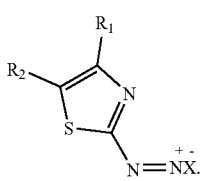
(VIII)

In some embodiments, $R_1$ and $R_2$ are each independently selected from an optionally substituted alkyl, an optionally substituted cycloalkyl, an optionally substituted alkoxy, a hydroxyl group, a halogen group, an amine group, a nitro group, and a cyano group; and X is a halogen. The nitrite salt is at least one selected from the group consisting of sodium nitrite, potassium nitrite, and lithium nitrite. In the preferred embodiment, the nitrite salt is sodium nitrite. In some embodiments, the molar ratio of the aminothiazole compound to the nitrite salt ranges from 1:1 to 1:10, preferably 1:8, preferably 1:6, preferably 1:4, or even more preferably 1:2. In a preferred embodiment, the diazotization is carried out preferably −5 to 2° C., more preferably −1 to 1° C., and yet more preferably 0° C. Other ranges are also possible.

According to an aspect of the present disclosure, a method of making a Schiff base is provided. The method includes mixing an aminothiazole compound having a formula (VII), and an aromatic aldehyde in the presence of a superparamagnetic iron oxide nanoparticles (SPIONs) catalyst thereby condensing the aromatic aldehyde with an amine group of the aminothiazole compound to form the Schiff base having a formula (IX).

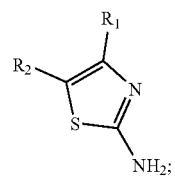
(VII)

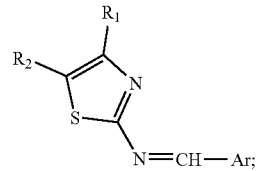
(IX)

In some embodiments, $R_1$ and $R_2$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group. In some further embodiments, Ar is selected from the group consisting of —$C_6H_5$, p-($C_6H_4$)—Cl, o-($C_6H_4$)—$NO_2$, p-($C_6H_4$)—OH, o-($C_6H_4$)—OH, p-($C_6H_4$)—OMe, o-($C_6H_4$)—OMe, 2,4-($C_6H_3$)—$(OMe)_2$, and 2,3-($C_6H_3$)—$(OMe)2$,2-methylindolyl-4-. The aromatic aldehyde is at least one aldehyde selected from the group consisting of benzaldehyde, p-chlorobenzaldehyde, o-nitrobenzaldehyde, p-hydroxybenzaldehyde, salicylaldehyde, p-anisaldehyde, o-anisaldehyde, 2,4-dimethoxy benzaldehyde, 2,3-dimethoxybenzaldehyde, and 2-methyl indolyl-3-carboxaldehyde. In some preferred embodiments, a molar ratio of the aminothiazole compound to the aromatic aldehyde is in a range of 1:1 to 1:3, more preferably about 1:2. Other ranges are also possible. In some more preferred embodiments, a molar ratio of the SPIONs catalyst having a formula $Fe_3O_4$ to the aminothiazole compound is in a range of 1:200 to 1:10, or more preferably about 1:100. Other ranges are also possible.

Referring to FIG. 6, in some embodiments, the method of making the Schiff base has a product yield in a range of 70 to 95% based on an initial amount of the aminothiazole compound, more preferably 80 to 90%. In some further embodiments, the method of making the Schiff base has a reaction time in a range of 30 to 90 minutes, more preferably 60 minutes. Other ranges are also possible.

In some embodiments, the Schiff base is at least one selected from the group consisting of N-(benzylidene)thiazol-2-amine, N-(4-chlorobenzylidene)thiazol-2-amine, N-(2-nitrobenzylidene)thiazol-2-amine, 4-((thiazol-2-ylimino)methyl)phenol, 2-((thiazol-2-ylimino)methyl)phenol, N-(4-methoxybenzylidene)thiazol-2-amine, N-(2-methoxybenzylidene)thiazol-2-amine, N-(2,4-dimethoxybenzylidene)-thiazol-2-yl-amine, N-(2,3-dimethoxybenzylidene)thiazol-2-amine, and N-((2-methyl-1H-indol-3-yl)methylene)thiazol-2-amine.

In some embodiments, the Schiff base can also inhibit microbial growth of at least one selected from the group consisting of *E. coli, P. aeruginosa, B. subtilis, S. aureus,* and *C. albicans*. The Schiff base may also inhibit microbial growth of *Campylobacter, Clostridium perfringens, Listeria, Norovirus, Salmonella, Deinococcus radiodurans, Myxococcus xanthus,* and *Yersinia pestis*.

FIG. 1B is a schematic flow chart of a method 80 of preparing the SPIONs catalyst. The order in which the method 80 described is not intended to be construed as a limitation, and any number of the described method steps can be combined in any order to implement the method 80. Additionally, individual steps may be removed or skipped from the method 80 without departing from the spirit and scope of the present disclosure.

At step 82, the method 80 includes mixing an iron (II) salt and an iron (III) salt in the water to form a mixture under an inert atmosphere. The mixing of the iron (II) salt and the iron (III) salt in the water to form the mixture may be performed under a nitrogen atmosphere with a continuous stirring speed in a range of 200 to 1000 rotations per minute (rpm), preferably 400 to 800 rpm, or even more preferably about 600 rpm. Other ranges are also possible. In some embodiments, The iron (II) salt includes iron (II) fluoride, iron (II) chloride, iron (II) bromide, and hydrates thereof. In a preferred embodiment, the iron (II) salt is iron (II) fluoride. In some embodiments, the iron (III) salt includes iron (III) fluoride, iron (III) chloride, iron (III) bromide, and its hydrate. Furthermore, in a preferred embodiment, the iron (III) salt is iron (III) fluoride. In some embodiments, a molar ratio of the iron (II) salt to the iron (III) salt in the mixture is 2:1 to 1:4, preferably 1:1 to 1:3, or even more preferably about 1:2. Other ranges are also possible. It is generally preferred to carry out this reaction in an inert atmosphere, such as Argon atmosphere, or nitrogen atmosphere, or a mix of both, to prevent oxidation of iron to its corresponding oxides.

At step 84, the method 80 includes heating the mixture to a temperature of 80 to 100° C., more preferably 85 to 95° C., and yet more preferably 90° C., and mixing with an ammonium hydroxide solution to form a reaction mixture having a pH of 8 to 10, more preferably 8.5 to 9.5, and yet more preferably 9. The ammonium hydroxide solution has an ammonia concentration of 15 to 30%, more preferably 22 to 26%, and yet more preferably 25%, by mass. Other ranges are also possible.

At step 86, the method 80 includes continuously agitating the reaction mixture to form the SPIONs as a precipitate. The main advantage of continuous agitation is to provide homogenization and uniformity. In some embodiments, the SPIONs are in the shape of spherical particles. The main advantage of a spherical shape is that spheres possess minimum surface area amongst all geometric shapes. Moreover, spherical shapes ensure the minimum possible state of energy in existence. The geometry of the SPIONs may include but is not limited to, a circular, polygonal, triangular, and rectangular. The SPIONs have an average diameter of 2 to 20 nanometers (nm), preferably 4 to 18 nm, preferably 6 to 16 nm, preferably 8 to 14 nm, and yet more preferably 10 to 12 nm. Other ranges are also possible.

At step 88, the method 80 includes removing the precipitate from the reaction mixture, washing, and drying from the SPIONs catalyst. The precipitate may be separated from the reaction mixture by methods including, but not limited to, filtration, decantation, and evaporation. The SPIONs may be superparamagnetism due to the presence of atoms. In the preferred embodiment, a magnet is used separates the precipitate from the reaction mixtures. Furthermore, the precipitate can be washed with ethanol or water. Moreover, the drying of the precipitate from the SPIONs catalyst can be done using heating appliances such as ovens, microwaves, autoclaves, hot plates, heating mantles and tapes, oil baths, salt baths, sand baths, air baths, hot-tube furnaces, and hot-air guns.

The crystalline structures of the SPIONs catalyst may be characterized by X-ray diffraction (XRD), respectively. In some embodiments, the XRD patterns are collected in a Rigaku diffractometer equipped with a Cu-Kα radiation source ($\lambda$=0.15406 nm) for a 2θ range extending between 5 and 80°, preferably 15 and 70°, further preferably 30 and 60° at an angular rate of 0.005 to 0.04° $s^{-1}$, preferably 0.01 to 0.03° $s^{-1}$, or even preferably 0.02° $s^{-1}$.

Figure 3A:
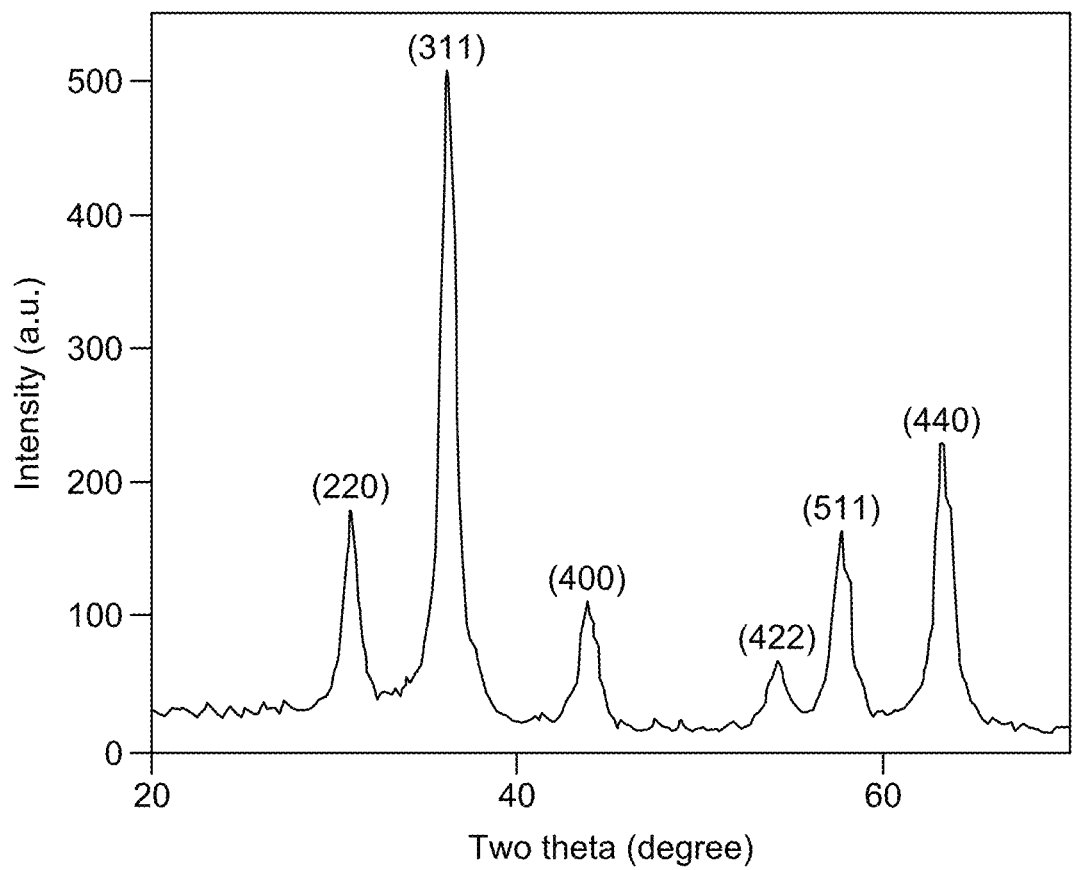
FIG. 3A depicts an X-ray diffraction (XRD) pattern for the $Fe_3O_4NPs$, according to certain embodiments.

FIG. 3A illustrates an X-ray diffraction (XRD) pattern for the SPIONs catalyst. In some embodiments, the SPIONs catalyst has a first intense peak with a 2 theta (θ) value in a range of 25 to 33° in an X-ray diffraction (XRD) spectrum, a second intense peak with a 2 theta (θ) value in a range of 33 to 38° in the XRD spectrum, a third intense peak with a 2 theta (θ) value in a range of 38 to 48° in the XRD spectrum, a fourth intense peak with a 2 theta (θ) value in a range of 48 to 55° in the XRD spectrum, a fifth intense peak with a 2 theta (θ) value in a range of 55 to 61° in the XRD spectrum, a sixth intense peak with a 2 theta (θ) value in a range of 61 to 68° in the XRD spectrum, as depicted in FIG. 3A. Other ranges are also possible.

EXAMPLES

The following examples describe and demonstrate exemplary embodiments of the method described herein. The examples are provided solely for the purpose of illustration and are not to be construed as limitations of the present disclosure, as many variations thereof are possible without departing from the spirit and scope of the present disclosure.

Example 1: Materials and Methods

The melting points were determined using the Stuart SMP30 Digital Advanced MP apparatus, and measured in an open capillary without correction. FTIR study was carried out on an infrared (IR) Affinity (FTIR) spectrometer from Shimadzu (manufactured by Shimadzu 2340-C Walsh Avenue, Santa Clara, California 95051, U.S.A). Sample were prepared on glass plates containing solid potassium bromide (KBr). Liquid chromatography-mass spectrometry (LC/MS) was recorded on an A LCMS-8040 spectroscopy (Shimadzu corporation, model CAT-30A, serial no. L20574900241 AE) operated at 220-240 volts (v), 50-60 Hz, and 300 volt-ampere (VA) ((manufactured by Shimadzu 2340-C Walsh Avenue, Santa Clara, California 95051, U.S.A). 1H NMR and $^{13}$C NMR were recorded on a 400-megahertz (MHz) BRUKER spectrometer (manufactured by Bruker, 40 Manning Road Billerica, MA 01821 United States). Samples were prepared by dissolution at DMSO $d_6$.

Chemical shifts (δ) are presented in part per million (ppm) using tetramethylsilane (TMS) as an internal standard. Elemental microanalyses were done on a Carlo Erba analyzer model 110 (manufactured by 168, 3rd Avenue, Waltham, Massachusetts, United States). XRD patterns were recorded on a Rigaku model Ultima-IV diffractometer employing Cu-Kα radiation ($\lambda$=1.5406 angstrom (A°)) at 40 kilovolts (kV) and 25 milliamperes (mA) over a 2θ range between 20 and 80°. All XRD measurement is handled in the air atmosphere. Samples for SEM were prepared from ethanolic suspensions on single-sided alumina tape placed on alumina stubs. For elemental analysis and mapping, energy-dispersive X-ray spectra (EDS) were collected on a Lyra 3 (manufactured from TESCAN ORSAY HOLDING, a.s . . . . Libušina tř. 21 623 00 Brno-Kohoutovice Czech Republic) attachment to the SEM. TEM micrographs were obtained from a high-resolution transmission electron microscopy (HRTEM) (JEOL JEM-2100F) equipped with an energy-dispersive X-ray spectrometer (EDX) operated at 200 kV. 300 mesh copper grids coated with carbon films were used for the imaging. The TEM samples were prepared by dropping them on a copper grid from an ethanolic suspension and drying them at room temperature.

Example 2: Synthesis of Nanomagnetic Catalyst

Figure 2:
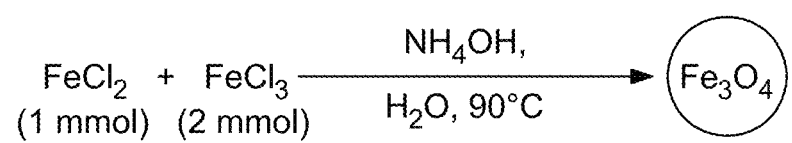
FIG. 2 is a schematic diagram depicting a synthesis of $Fe_3O_4$ nanoparticles (NPs), according to certain embodiments.

Magnetic nanoparticles having a particle size in a range of 6-8 nm were prepared. FIG. 2 shows a synthetic route for the magnetic nanoparticles. In a 250 milliliter (ml) round bottom flask, hydrated ferrous chloride ($FeCl_2 \cdot H_2O$) (5 mmol, 1 g) and ferric chloride ($FeCl_3 \cdot H_2O$) (10 millimoles (mmol), 4.04 grams (g)) were dissolved in de-ionized water (DI—$H_2O$) (100 ml) under nitrogen atmosphere with a continuous stirring speed of 600 rpm. Then $NH_4OH$ (25%) solution (25 ml) was added slowly at 90° C. to raise the pH to 9. An orange color solution turned into black in 15 minutes and was kept stirring for another 3 h to complete the reduction. The mixture was allowed to precipitate and collected using a simple magnet. The black solid was washed several times (5×25 ml) to remove the unreacted metal precursors and ammonia. Powdered material was dried and used for characterization and catalytic reaction.

Example 3: Synthesis of 2-(Chlorodiazenyl)Thiazole (2)

Dissolve (1 mmol) of 2-aminothiazole (1) in 3 ml of HCl. Keep this solution in ice at 0° C. Then, diazotize this solution using $NaNO_2$ (5 mmol) solution (prepared by dissolving 5 mmol of $NaNO_2$ in 1 ml $H_2O$). The reaction mixture was kept in an ice bath for 3 h to give compound (2) as a pink powder; yield (89.78%), mp.: 126.7° C. FT-IR (KBr, v, $cm^{-1}$): absence of ($NH_2$), 3010, the appearance of 2980 (CH), and 1530 (N=N); $^1$H NMR: (400 MHZ, DMSO $d_6$, δ, ppm), 6.90 (d, 1H, J=8.0 Hz, H-2-thiazole), 7.27 (d, 1H, J=8.0 Hz, H-3-thiazole); $^{13}$C NMR: (400 MHZ, DMSO $d_6$, δ, ppm): 170.1 (S—C—N), 150.4 (C=N thiazolyl), 127.0, 108.3 (C-thiazolyl); MS (m/z): 146.98 (M$^+$, 80.5%); Anal. calcd. for $C_3H_2ClN_3S$ (146.96): C, 24.41; H, 1.37; Cl, 24.02; N, 28.47; S, 21.73%; found: C, 24.93; H, 1.39; Cl, 24.00; N, 28.45; S, 21.77%.

Example 4: Coupling with Active Methylene Compounds (3-5)

Reflux an equivalent amount of (2) (1 mmol) and (1 mmol) ethyl acetoacetate, ethyl cyanoacetate, and acetylacetone, respectively, in the presence of 25 ml ethanol for 1 h. The solid formed was recrystallized from ethanol to give (3-5) respectively.

Ethyl 3-oxo-2-(thiazol-2yldiazenyl)butanoate (3)
Light orange powder; yield (60.78%), mp.: 135.4° C.; FT-IR (KBr, v, $cm^{-1}$): 3010, 2980 (CH), 1750 (C=O ester and ketone) and 1590 (C=N); $^1$H NMR: (400 MHZ, DMSO $d_6$, δ, ppm): 1.35, 2.08 (m, 3H, 2CH$_3$), 4.11 (m, 2H, —CH$_2$—), 4.70 (s, 1H, CH—N); 7.16 (d, 1H, J=8.0 Hz, H-2-thiazole), 7.55 (d, 1H, J=8.0 Hz, H-3-thiazole), $^{13}$C NMR: (400 MHZ, DMSO $d_6$, δ, ppm): 171.0 (C=O ester), 166.9 (C=O), 150.4 (C=N thiazolyl), 125.0, 119.8 (C-thiazolyl), 62.9 (C—N), 13.6, 20.0 (CH$_3$); 59.2 (CH$_2$); MS (m/z): 240.05 (M$^+$-1, 11.33%); Anal. calcd. for $C_9H_{11}N_3O_3S$ (241.05): C, 44.80; H, 4.60; N, 17.42; S, 13.29%; found: C, 43.93; H, 4.44; N, 17.45; S, 13.39%.

Ethyl 2-cyano-2-(thiazol-2-yldiazenyl)acetate (4)
Orange powder; yield (65.45%), mp.: 144.3° C.; FT-IR (KBr, v, $cm^{-1}$): 3010, 2980 (CH), 1749 (C=O), 1590 (C—N), 2260-2222 (CN); $^1$H NMR: (400 MHZ, DMSO $d_6$, δ, ppm): 1.65 (s, 3H, CH$_3$), 2.12 (m, 3H, —CH$_2$—), 7.15 (d, 1H, J=8.0 Hz, H-2-thiazole), 7.5 (d, 1H, J=8.0 Hz, H-3-thiazole); $^{13}$C NMR: (400 MHZ, DMSO $d_6$, δ, ppm): 171.1 (C=O), 152.4 (C=N thiazolyl), 125.0, 119.7 (CH-thiazolyl), 114.9 (CN), 50.9 (C—N), 58.7 (—CH$_2$), 22.9 (CH$_3$); MS (m/z): 224.04 (M$^+$, 11.69%); Anal. calcd. for $C_8H_8N_4O_2S$ (224.04): C, 42.85; H, 3.60; N, 24.99; S, 14.30%; found: C, 42.55; H, 3.68; N, 25.10; S, 14.40%.

3-(Thiazol-2-yl-hydrazono)-pentane-2,4-dione (5)
Yellow powder; yield (60.02%), mp.: 165.2° C.; FT-IR (KBr, v, $cm^{-1}$): 3010, 2980 (CH), 1750 (C—O) and 1590 (C=N); $^1$H NMR: (400 MHZ, DMSO $d_6$, δ, ppm): 2.09 (s, 6H, 2CH$_3$), 7.15 (d, 1H, J=8.0 Hz, H-2-thiazole), 7.51 (d, 1H, J=8.0 Hz, H-3-thiazole); $^{13}$C NMR: (400 MHZ, DMSO $d_6$, δ, ppm): 206.0 (C=O), 85.7 (C=N), 151.4 (C=N thiazolyl), 125.0, 119.7 (C-thiazolyl), 19.3 (CH$_3$); MS (m/z): 211.24 (M$^+$, 22.01%); Anal. calcd. for $C_8H_9N_3O_2S$ (211.24): C, 45.49; H, 4.29; N, 19.89; O, 15.15; S, 15.18%; found: C, 46.10; H, 4.32; N, 19.69; O, 15.05; S, 15.08%.

Example 5: Synthesis of Pyrazol-5-One Derivatives (6-8)

An equivalent mixture of (1 mmol) of (3-5) and (2 mmol) hydrazine hydrate in the presence of (0.01 mmol) of $Fe_3O_4$, the reaction mixture was stirred for 2 h at room temperature. The solid formed was recrystallized from ethanol to give (6-8) respectively.

3-methyl-4-(thiazol-2-yldiazenyl)-1H-pyrazol-5(4H)-one (6)
Beige powder; yield (87.02%), mp.: 155.5° C.; FT-IR (KBr, v, $cm^{-1}$): 3250 (NH), 3010, 2980 (CH), 1750 (C=O) and 1590 (C=N); $^1$H NMR: (400 MHz, DMSO $d_6$, δ, ppm): 1.75 (s, 3H, CH$_3$), 7.16 (d, 1H, J=8.0 Hz, H-2-thiazole), 7.55 (d, 1H, J=8.0 Hz, H-3-thiazole), 8.70 (s, 1H, NH-pyrazolyl); $^{13}$C NMR: (400 MHZ, DMSO $d_6$, δ, ppm): 166.9 (C=O), 156.7 (C=N pyrazolyl), 150.4 (C=N thiazolyl), 125.0, 119.7 (C-thiazolyl), 62.9 (C—N), 22.9 (CH$_3$); MS (m/z): 209.06 (M$^+$, 55.05%); Anal. calcd. for $C_7H_7N_5OS$ (209.04): C, 40.18; H, 3.37; N, 33.47; S, 15.33%; found: C, 41.00; H, 3.26; N, 33.27; S, 15.13%.

3-amino-4-(thiazol-2-yldiazenyl)-1H-pyrazol-5(4H)-one (7)
Orange powder; yield (80.66%), mp.: 172.0° C.; FT-IR (KBr, v, $cm^{-1}$): 3330, 3250 (NH$_2$, NH), 3010, 2850 (CH), 1715 (C=O) and 1600 (C=N); $^1$H NMR: (400 MHZ, DMSO $d_6$, δ, ppm): 1.81 (s, 3H, CH$_3$), 7.69 (d, 1H, J=8.0 Hz, H-2-thiazole), 7.88 (d, 1H, J=8.0 Hz, H-3-thiazole), 8.26 (s, 1H, NH-pyrazolyl), 8.54 (s, 1H, NH$_2$); $^{13}$C NMR: (400 MHZ, DMSO $d_6$, δ, ppm): 163.3 (C=O), 159.2 (C=N pyrazolyl), 140.9 (C=N pyrazolyl), 140.0 (C-thiazolyl), 62.9 (C—N), 15.4 (CH$_3$); MS (m/z): 210.01 (M$^+$, 33.2%); Anal. calcd. for $C_6H_6N_6OS$ (210.03): C, 34.28; H, 2.88; N, 39.98; S, 15.25%; found: C, 33.20; H, 2.90; N, 40.00; S, 15.35%.

(3,5-Dimethyl-4H-pyrazol-4-yl)-thiazol-2-yl-diazene (8)
Yellow powder; yield (82.03%), mp.: 186.0° C.; FT-IR (KBr, v, $cm^{-1}$): 3380 (NH), 3010, 2850 (CH, CH$_3$), and 1600 (C,N); $^1$H NMR: (400 MHZ, DMSO $d_6$, δ, ppm): 2.01 (s, 6H, 2CH$_3$), 7.46 (d, 1H, J=8.0 Hz, H-2-thiazole), 8.00 (d, 1H, J=8.0 Hz, H-3-thiazole), 8.00 (s, 1H, NH-pyrazolyl); $^{13}$C NMR: (400 MHZ, DMSO $d_6$, δ, ppm): 164.5 (C=N pyrazolyl), 33.4 (C=N pyrazolyl), 153.0, 143.0 (C-thiazolyl), 62.9 (C—N), 15.4 (CH$_3$); MS (m/z): 207.10 (M$^+$, 22.11%); Anal. calcd. for $C_8H_9N_5S$ (207.06): C, 46.36; H, 4.38; N, 33.79; S, 15.47%; found: C, 45.49; H, 4.40; N, 33.81; S, 15.45%.

Example 6: Procedure for Schiff Bases Synthesis of Compounds (9-18)

An equivalent amount of (1 mmol) of 1 and various aromatic aldehydes (1 mmol), namely: benzaldehyde, p-chlorobenzaldehyde, o-nitrobenzaldehyde, p-hydroxybenzaldehyde, salicylaldehyde, p-/o-anisaldehyde, 2, 4-/2,3-dimethoxybenzaldehyde, and 2-methyl indolyl-3-carboxaldehyde in the presence of (0.01 mmol) of $Fe_3O_4$, reaction medium at room temperature (RT) for 1 h. The solid formed was recrystallized from ethanol to give the corresponding Schiff bases derivatives (9-18).

N-(benzylidene)thiazol-2-amine (9)

Yellow powder; yield (81.00%), mp.: 113-115° C.; FT-IR (KBr, v, cm$^{-1}$): absence of (C=O, NH$_2$), 3020, 2990 (CH), 1590 (C=N); $^1$H NMR: (400 MHZ, DMSO d$_6$, δ, ppm): 7.37-7.74 (m, 5H, CH-aromatic), 7.54 (d, 1H, J=8.0 Hz, H-4-thiazole), 7.20 (d, 1H, J=8.0 Hz, H-5-thiazole), 9.01 (s, 1H, CH=N); $^{13}$C NMR: (400 MHZ, DMSO d$_6$, δ, ppm): 171.9 (N=C—S), 167.1 (HC=N), 141.6, 119.8 (C-thiazolyl), 127.8, 124.4, 123.9 (C-aromatic); MS(m/z): 188.10 (M$^+$, 44.05%); Anal. calcd. for $C_{10}H_8N_2S$ (188.04): C, 63.80; H, 4.28; N, 14.88; S, 17.03%; found: C, 63.76; H, 4.20; N, 14.91; S, 17.13%.

N-(4-chlorobenzylidene)thiazol-2-amine (10)

Brown crystal; yield (88.05%), mp.: 134.8° C.; FT-IR (KBr, v, cm$^{-1}$): absence of (C=O, NH$_2$), 3010, 2990 (CH), 1580 (C=N); $^1$H NMR: (400 MHZ, DMSO d$_6$, δ, ppm): 7.66-8.02 (m, 4H, CH-aromatic), 7.60 (d, 1H, J=8.0 Hz, H-4-thiazole), 6.65 (d, 1H, J=8.0 Hz, H-5-thiazole), 8.03 (s, 1H, CH=N); $^{13}$C NMR: (400 MHZ, DMSO d$_6$, δ, ppm): 171.9 (N=C—S), 166.6 (HC=N), 141.7, 119.9 (C-thiazolyl), 131.2, 129.7, 128.8 (C-aromatic); MS (m/z): 222.00 (M$^+$, 18.52%); Anal. calcd. for $C_{10}H_7ClN_2S$ (222.00): C, 53.93; H, 3.17; Cl, 15.92; N, 12.58; S, 14.40%; found: C, 53.83; H, 3.20; Cl, 15.99; N, 12.50; S, 14.51%.

N-(2-nitrobenzylidene)thiazol-2-amine (11)

Orange powder; yield (80.97%), mp.: 163.5° C.; FT-IR (KBr, v, cm$^{-1}$): absence of (C,O, NH$_2$), 3020, 2990 (CH), 1610 (C,N); $^1$H NMR: (400 MHZ, DMSO d$_6$, δ, ppm): 6.54-7.76 (m, 4H, CH-aromatic), 7.02 (d, 1H, J=8.0 Hz, H-4-thiazole), 7.01 (d, 1H, J=8.0 Hz, H-5-thiazole), 8.51 (s, 1H, CH=N); $^{13}$C NMR: (400 MHZ, DMSO d$_6$, δ, ppm): 166.8 (N=C—S), 148.6 (HC=N), 134.4, 110.7 (C-thiazolyl), 134.2, 130.5, 129.0, 124.4 (C-aromatic); MS(m/z): 233.02 (M$^+$, 80%); Anal calcd. for $C_{10}H_7N_3O_2S$ (233.03): C, 51.49; H, 3.02; N, 18.02; S, 13.75%; found: C, 51.55; H, 3.32; N, 18.12; S, 13.75%.

4-((thiazol-2-ylimino)methyl)phenol (12)

Yellow powder; yield (85.43%), mp.: 175.2° C.; FT-IR (KBr, v, cm$^{-1}$): absence of (C=O, NH$_2$), 3020, 2890 (CH), 1605 (C=N); $^1$H NMR: (400 MHZ, DMSO d$_6$, δ, ppm): 6.38-7.33 (m, 4H, CH-aromatic), 7.07 (d, 1H, J=8.0 Hz, H-4-thiazole), 7.72 (d, 1H, J=8.0 Hz, H-5-thiazole), 8.27 (s, 1H, CH=N), 9.84 (s, 1H, OH); $^{13}$C NMR: (400 MHZ, DMSO d$_6$, δ, ppm): 173.0 (N=C—S), 162.2 (HC=N), 141.3, 115.9 (C-thiazolyl), 138.6, 132.1, 116.1 (C-aromatic); MS (m/z): 206.05 (M$^+$+2, 23.07%); Anal. calcd. for $C_{10}H_8N_2OS$ (204.04): C, 58.80; H, 3.95; N, 13.72; S, 15.70%; found: C, 58.92; H, 3.98; N, 13.75; S, 15.75%.

2-((thiazol-2-ylimino)methyl)phenol (13)

Brown powder; yield (90.00%), mp.: 165.8° C.; FT-IR (KBr, v, cm$^{-1}$): absence of (C—O, NH$_2$), 3320 (OH), 3010, 2880 (CH), 1610 (C=N); $^1$H NMR: (400 MHz, DMSO d$_6$, δ, ppm): 10.25 (s, 1H, OH), 6.92-8.54 (m, 4H, CH-aromatic), 7.64 (d, 1H, J=8.0 Hz, H-4-thiazole), 7.01 (d, 1H, J=8.0 Hz, H-5-thiazole), 8.21 (s, 1H, CH,N); $^{13}$C NMR: (400 MHZ, DMSO d$_6$, δ, ppm): 160.8 (N=C—S), 154.3 (HC—N), 122.3, 119.5, 119.5 (C-aromatic); MS (m/z): 204.04 (M$^+$, 55.01%); Anal. calcd. for $C_{10}H_8N_2OS$ (204.04): C, 58.80; H, 3.95; N, 13.72; S, 15.70%; found: C, 58.78; H, 3.75; N, 13.62; S, 15.68%.

N-(4-methoxybenzylidene)thiazol-2-amine (14)

Yellow powder; yield (87.07%), mp.: 102-103° C.; FT-IR (KBr, v, cm$^{-1}$): absence of (C=O, NH$_2$), 3020, 2990 (CH), 1610 (C=N); $^1$H NMR: (400 MHZ, DMSO d$_6$, δ, ppm): 6.35-7.31 (m, 4H, CH-aromatic), 7.60 (d, 1H, J=8.0 Hz, H-4-thiazole), 7.21 (d, 1H, J=8.0 Hz, H-5-thiazole), 8.12 (s, 1H, CH=N), 3.38 (s, 6H, OCH$_3$); $^{13}$C NMR: (400 MHZ, DMSO d$_6$, δ, ppm): 161.5 (N=C—S), 156.0 (H—C=N), 135.5, 120.6 (C-thiazolyl), 129.5, 128.4, 126.1 (C-aromatic), 62.9, 55.8 (OCH$_3$); MS (m/z): 218.10 (M$^+$, 60.0%); Anal. calcd. for $C_{11}H_{10}N_2OS$ (218.05): C, 60.53; H, 4.62; N, 12.83; S, 14.69%; found: C, 60.71; H, 4.66; N, 12.88; S, 14.72%.

N-(2-methoxybenzylidene)thiazol-2-amine (15)

Orange powder; yield (90.05%), mp.: 150.9° C.; FT-IR (KBr, v, cm$^{-1}$): absence of (C=O, NH$_2$), 3009, 2890 (CH), 1605 (C,N); $^1$H NMR: (400 MHZ, DMSO d$_6$, δ, ppm): 6.37-7.21 (m, 4H, CH-aromatic), 7.60 (d, 1H, J=8.0 Hz, H-4-thiazole), 7.21 (d, 1H, J=8.0 Hz, H-5-thiazole), 8.12 (s, 1H, CH=N), 3.33 (s, 6H, OCH$_3$); $^{13}$C NMR: (400 MHZ, DMSO d$_6$, δ, ppm): 161.5 (N=C—S), 156.0 (HC—N), 135.5, 120.6 (C-thiazolyl), 129.5, 128.5, 126.1 (C-aromatic), 62.9, 55.8 (OCH$_3$); MS (m/z): 218.10 (M$^+$, 66.03%); Anal. calcd. for $C_{11}H_{10}N_2OS$ (218.05): C, 60.53; H, 4.62; N, 12.83; S, 14.69%; found: C, 60.73; H, 4.74; N, 11.93; S, 13.99%.

N-(2,4-dimethoxy-benzylidene)-thiazol-2-yl-amine (16)

Orange powder; yield (87.50%), mp.: 135.2° C.; FT-IR (KBr, v, cm$^{-1}$): absence of (C=O, NH$_2$), 3020, 2990 (CH), 1590 (C=N); $^1$H NMR: (400 MHZ, DMSO d$_6$, δ, ppm): 7.37-7.67 (m, 3H, CH-aromatic), 7.60 (d, 1H, J=8.0 Hz, H-4-thiazole), 7.20 (d, 1H, J=8.0 Hz, H-5-thiazole), 9.01 (s, 1H, CH=N), 3.49 (s, 6H, 2CH$_3$); $^{13}$C NMR: (400 MHZ, DMSO d$_6$, δ, ppm): 173.6 (N=C—S), 167.1 (HC=N), 141.7, 119.7 (C-thiazolyl), 126.9, 124.5, 123.7 (C-aromatic), 62.8, 55.8 (OCH$_3$); MS (m/z): 188.10 (M$^+$, 88.01%); Anal. calcd. for $C_{12}H_{12}N_2O_2S$ (248.06): C, 58.05; H, 4.87; N, 11.28; S, 12.91%; found: C, 59.04; H, 4.86; N, 11.29; S, 12.90%.

N-(2,3-dimethoxybenzylidene)thiazol-2-amine (17)

Yellow powder; yield (89.09%), mp.: 152.0° C.; FT-IR (KBr, v, cm$^{-1}$): absence of (C=O, NH$_2$), 3020, 2990 (CH), 1609 (C=N); $^1$H NMR: (400 MHZ, DMSO d$_6$, δ, ppm): 7.37-7.64 (m, 3H, CH-aromatic), 7.64 (d, 1H, J=8.0 Hz, H-4-thiazole), 7.20 (d, 1H, J=8.0 Hz, H-5-thiazole), 9.29 (s, 1H, CH=N), 3.44 (s, 6H, 2CH$_3$); $^{13}$C NMR: (400 MHZ, DMSO d$_6$, δ, ppm): 172.6 (N=C—S), 167.1 (HC—N), 141.6, 119.8 (C-thiazolyl), 127.9, 124.5, 123.9 (C-aromatic), 62.8, 55.8 (OCH$_3$); MS (m/z): 248.10 (M$^+$, 100%); Anal. calcd. for $C_{12}H_{12}N_2O_2S$ (248.06): C, 58.05; H, 4.87; N, 11.28; S, 12.91%; found: C, 59.05; H, 4.89; N, 11.30; S, 12.71%.

N-((2-methyl-1H-indol-3-yl)methylene)thiazol-2-amine (18)

Yellow powder; yield (86.34%), mp.: 180.2° C.; FT-IR (KBr, v, cm$^{-1}$): absence of (C—O, NH$_2$), 3010, 2980 (CH), 1600 (C=N); $^1$H NMR: (400 MHZ, DMSO d$_6$, δ, ppm): 11.99 (s, 1H, NH-indolyl), 7.13-8.02 (m, 4H, CH-aromatic), 7.16 (d, 1H, J=8.0 Hz, H-4-thiazole), 7.14 (d, 1H, J=8.0 Hz, H-5-thiazole), 8.04 (s, 1H, CH=N), 2.67 (s, 3H, CH$_3$); $^{13}$C NMR: (400 MHZ, DMSO d$_6$, δ, ppm): 184.1 (N—C=S), 148.5, 111.4 (C-thiazolyl), 150.0 (HC=N), 135.3, 125.6, 122.6, 121.8, 119.9, 113.6 (C-aromatic); MS (m/z): 241.10 (M$^+$, 66.09%); Anal. calcd. for C$_{13}$H$_{11}$N$_3$S (241.07): C, 64.70; H, 4.59; N, 17.41; S, 13.29%; found: C, 64.55; H, 4.48; N, 17.38; S, 13.31%.

Example 7: Characterizations

Figure 3B:
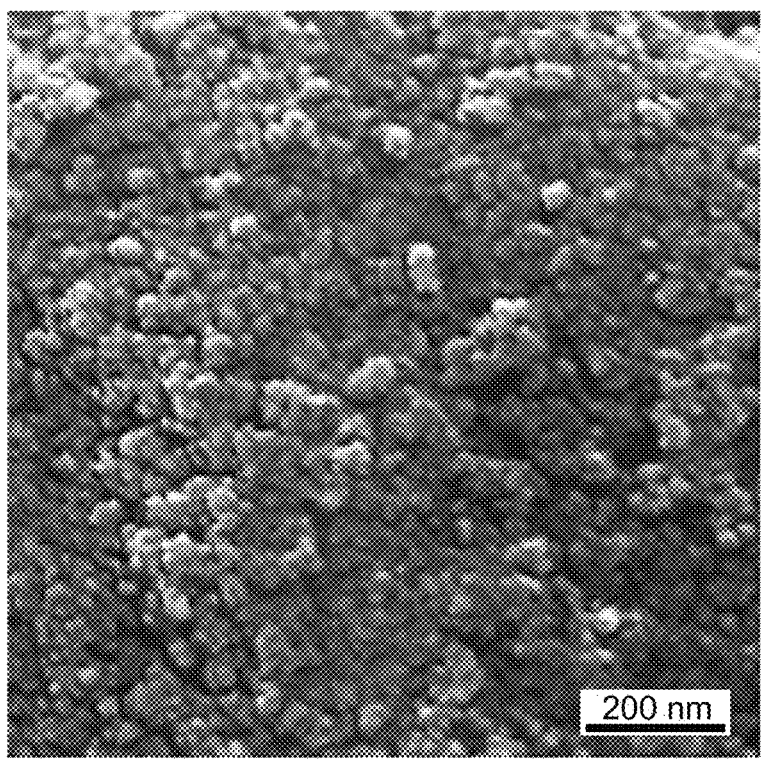
FIG. 3B depicts a scanning electron microscope (SEM) image of the $Fe_3O_4NPs$, according to certain embodiments.
Figure 3C:
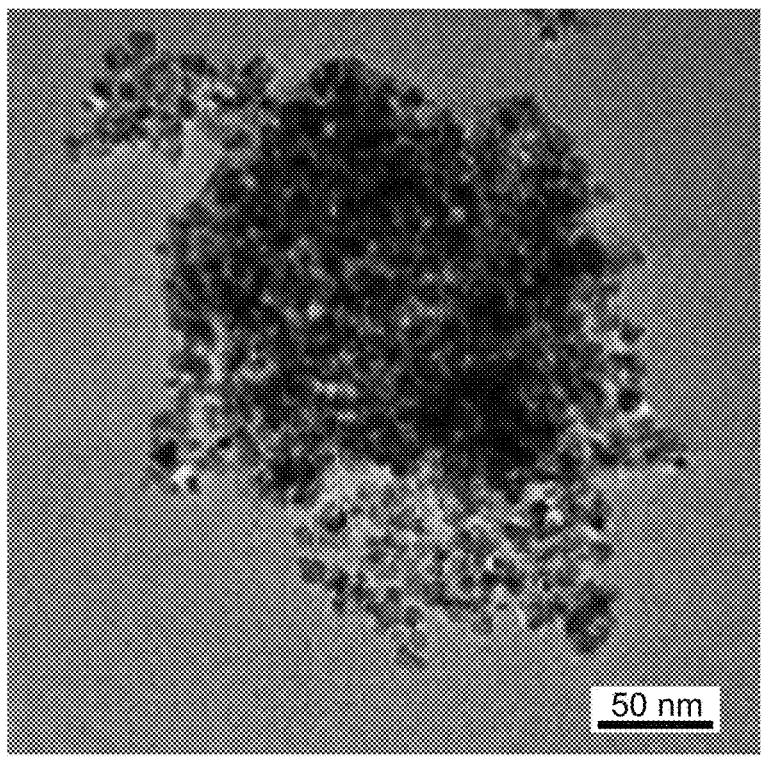
FIG. 3C depicts a transmission electron microscopy (TEM) image of the $Fe_3O_4NPs$, according to certain embodiments.
Figure 4:
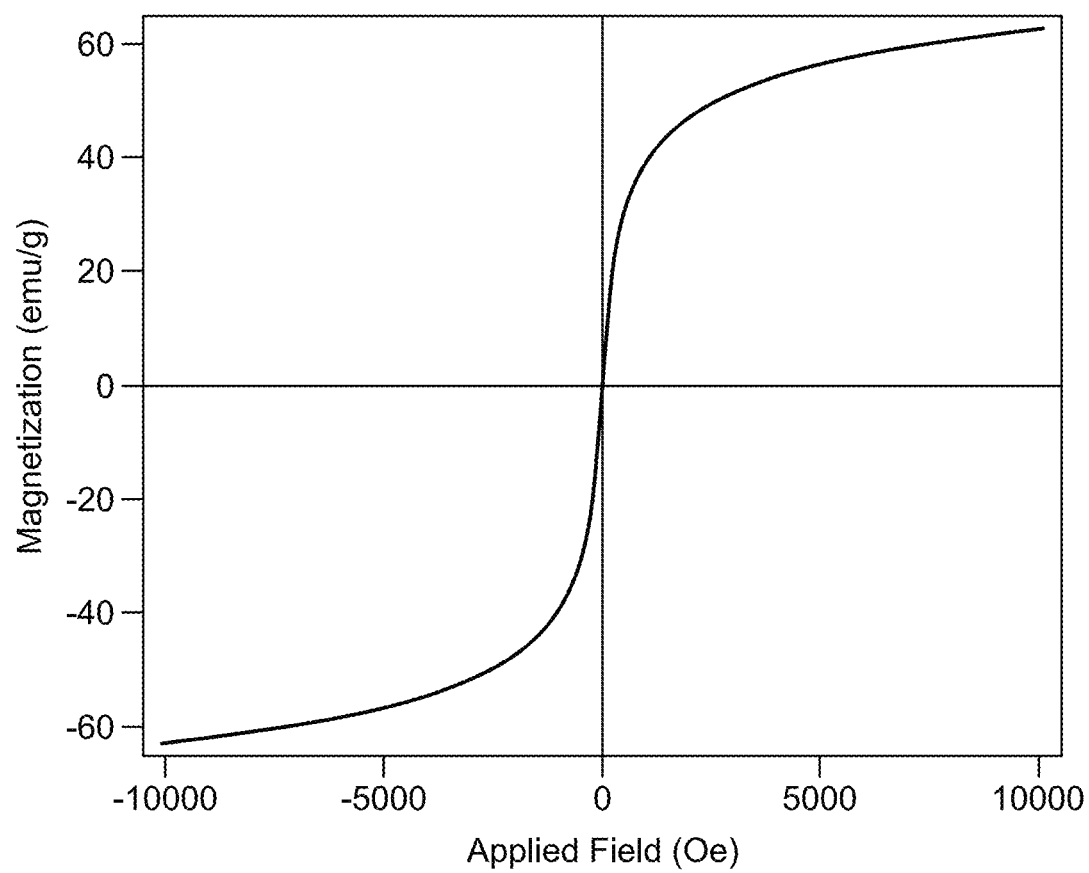
FIG. 4 depicts magnetic hysteresis loops of the $Fe_3O_4$ at room temperature with 1 Tesla magnet, according to certain embodiments.

Ultrasmall nanomagnetic catalysts are prepared by the co-precipitation technique using Fe(II) and Fe(III) as precursors and NH$_4$OH as reductant. Black powdered materials are collected by a magnet, and non-magnetic materials are removed by washing with water repeatedly (FIG. 2). The XRD signature confirms the crystallinity of the prepared nanocatalyst. The XRD patterns of Fe$_3$O$_4$ display characteristic peaks at 2θ 30.2, 35.7, 43.1, 53.4, 57.1, and 63.2, indicating the formation of crystalline cubic (Fd3m) spinnel structure (JCPDS card no. 01-075-0449). SEM images demonstrated highly agglomerated particles with extremely smaller-sized particles with smooth surfaces. The higher surface interaction among the bared surface ultrasmall nanoparticles leads to aggregation of the particles. TEM images show spherically shaped, uniformly distributed, nano-sized particles with 6-8 nm diameter, FIGS. 3A-3C. The magnetization field (M-H) curve is recorded at room temperature using PMC Micromag 3900 model vibrating sample magnetometer (VSM) equipped with a 1 Tesla magnet. The magnetic measurement of the Fe$_3$O$_4$NPs shows 62.69 emu g$^{-1}$, making them susceptible to separation using a simple magnet at the bottom of a vessel after the reaction, FIG. 4.

Figure 5:
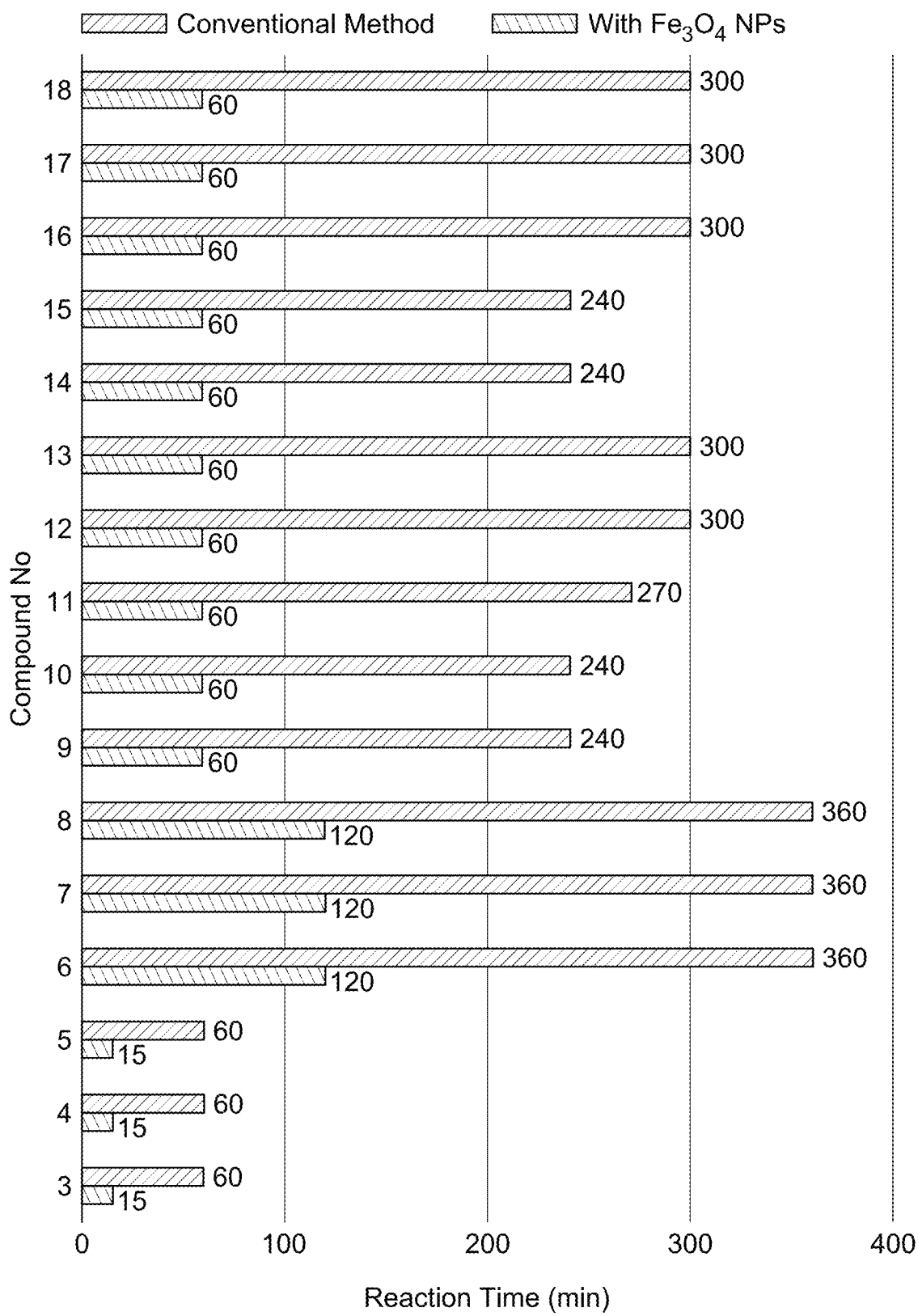
FIG. 5 is a plot depicting a reaction time of products, using conventional methods and with the $Fe_3O_4NPs$ catalysis, according to certain embodiments.

Nanomagnetic catalysis can be used for preparing organic compounds. Conventionally, the coupling of diazotization of amino heterocyclic compounds with various require conditions such as long raction period (>2 hours), and high reaction temperature. Herein, nanomagnetic catalysis (Fe$_3$O$_4$NPs) was used in coupling the diazonium salt of 2-aminothiazole with various active methylene compounds; the reaction was completed in 1 h. In addition to the short reaction time, it affords higher yields than the conventional method. FIG. 5 and FIG. 6 represent the pathway of preparing the target compounds. Coupling diazonium salt of 2-aminothiazole with ethyl acetoacetate, ethyl cyanoacetate, and acetylacetone in the presence of a catalytic amount of Fe$_3$O$_4$NPs at room temperature afforded the corresponding coupling products (3-5) as shown in Table 1, respectively in 1 h.

TABLE 1

Reaction intermediate and product list (3-18)

| Compound Number | IUPAC Name |
|---|---|
| 3 | Ethyl 3-oxo-2-(thiazol-2yldiazenyl)butanoate |
| 4 | Ethyl 2-cyano-2-(thiazol-2-yldiazenyl)acetate |
| 5 | 3-(Thiazol-2-yl-hydrazono)-pentane-2,4-dione |
| 6 | 3-methyl-4-(thiazol-2-yldiazenyl)-1H-pyrazol-5(4H)-one |
| 7 | 3-amino-4-(thiazol-2-yldiazenyl)-1H-pyrazol-5(4H)-one |
| 8 | (3,5-Dimethyl-4H-pyrazol-4-yl)-thiazol-2-yl-diazene |
| 9 | N-(benzylidene)thiazol-2-amine |
| 10 | N-(4-chlorobenzylidene)thiazol-2-amine |
| 11 | N-(2-nitrobenzylidene)thiazol-2-amine |
| 12 | 4-((thiazol-2-ylimino)methyl)phenol |
| 13 | 2-((thiazol-2-ylimino)methyl)phenol |
| 14 | N-(4-methoxybenzylidene)thiazol-2-amine |
| 15 | N-(2-methoxybenzylidene)thiazol-2-amine |
| 16 | N-(2,4-dimethoxy-benzylidene)-thiazol-2-yl-amine |
| 17 | N-(2,3-dimethoxybenzylidene)thiazol-2-amine |
| 18 | N-((2-methyl-1H-indol-3-yl)methylene)thiazol-2-amine |

Figure 7:
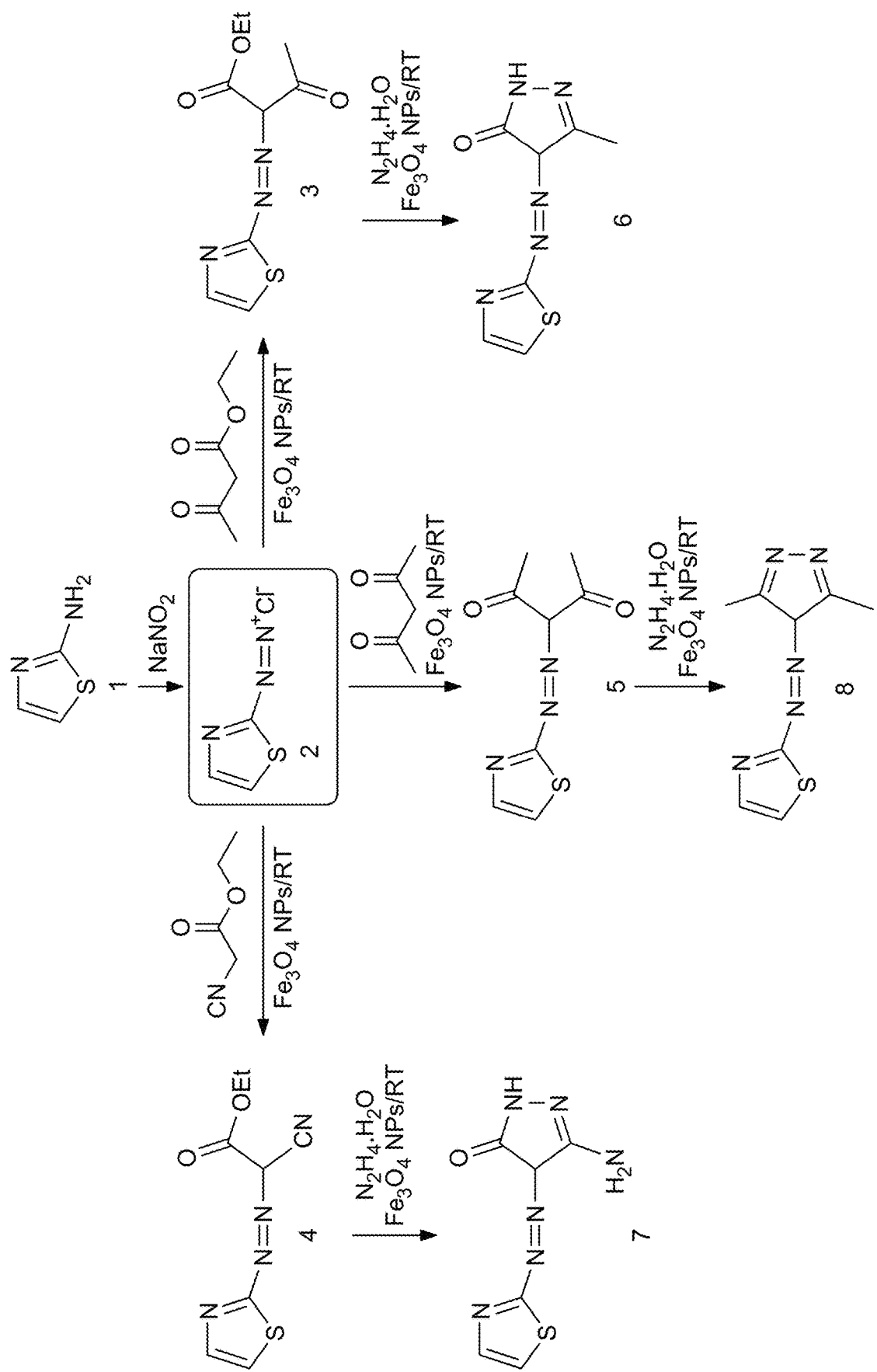
FIG. 7 is a schematic pathway depicting a synthesis of pyrazole derivatives, according to certain embodiments.
Figure 8:
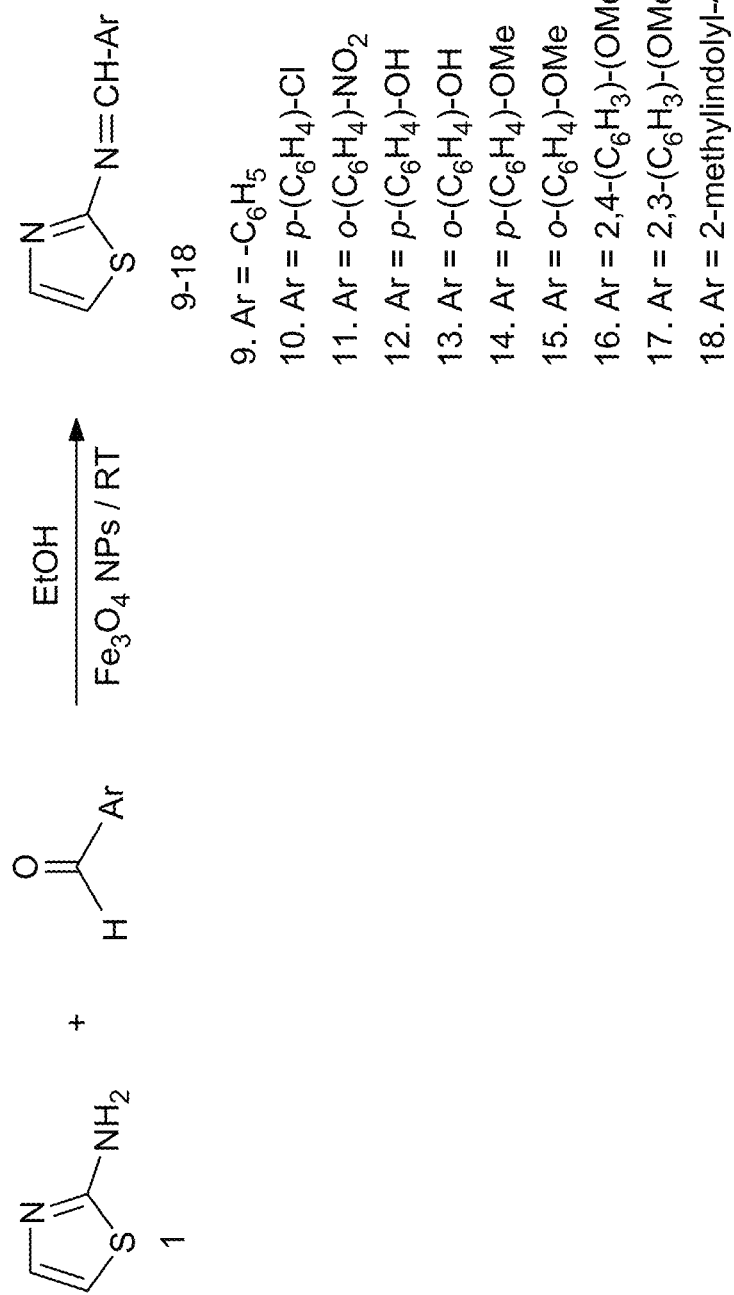
FIG. 8 is a schematic pathway depicting the synthesis of Schiff bases derivatives, according to certain embodiments.
Figure 9:
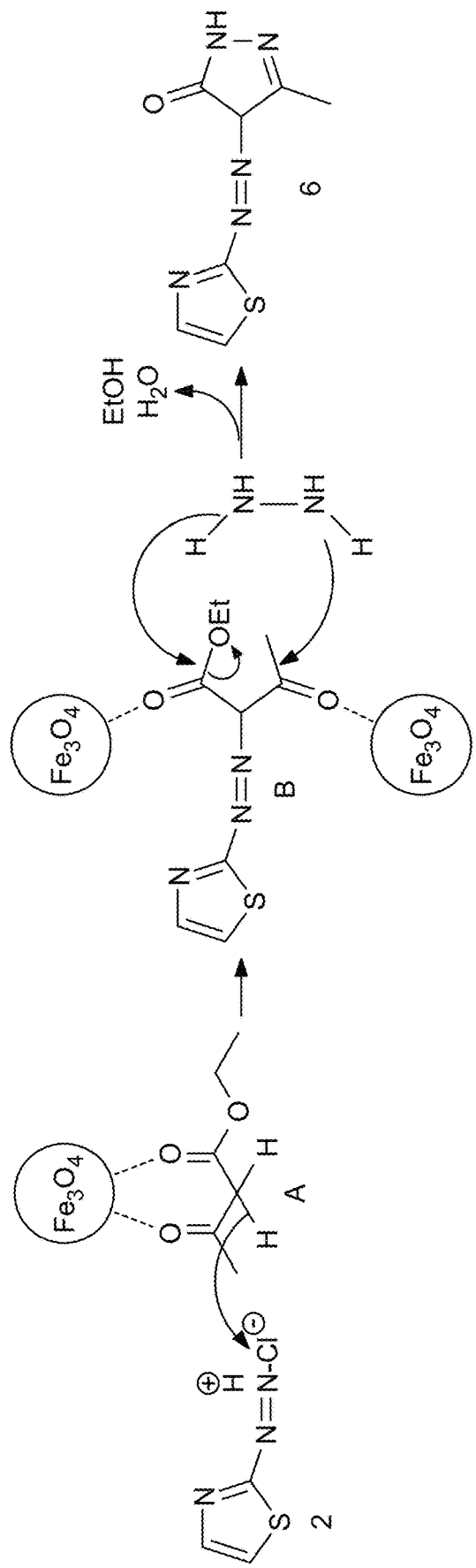
FIG. 9 is a plausible mechanism for synthesizing the pyrazole derivative, using the $Fe_3O_4NPs$, according to certain embodiments.

The reaction was monitored using the thin-layer chromatography (TLC) technique. The prepared compounds were proved via their cyclization upon nucleophilic attack within by nucleophile hydrazine hydrate afforded the corresponding pyrazolyl derivatives (6-8) as shown in FIG. 7 and Table 1. These products were elucidated based on spectral data. The IR spectrum of (6) as shown in Table 1 displayed absorption bands in the region 1750 cm-1 due to C=O, and at 3330, 3250 attributable for NH$_2$ in 7 as shown in table 1. $^1$H NMR spectrum of (7) in Table 1, for example, recorded new signals at d 8.54, 8.26 ppm assigned for NH$_2$ and NH, respectively. Moreover, the formation of Schiff bases from 2-aminothiazole was carried out upon the one-pot method by treatment with various aromatic aldehydes in the presence of Fe$_3$O$_4$NPs catalysis at room temperature as shown in FIG. 8. The reaction vanished in less time and furnished high yield than the conventional method (FIG. 5 and FIG. 6). The structures of these products were assigned using spectral analysis. IR for all compounds showed the absence of C=O and NH$_2$. The plausible mechanism is consistent with the published art [Sadeghi, M., Safari, J., Zarnegar, Z., 2016. Synthesis of 2-aminoth-iazoles from methylcarbonyl compounds using a Fe$_3$O$_4$ nanoparticle-N-halo reagent catalytic system. RSC Adv. 6, 64749-64755; Zolfigol, M. A., Khakyzadeh, V., Moosavi-Zare, A. R., Zare, A., Arghavani-Hadi, P., Mohammadi, Z., Beyzavi, M. H., 2012. Nano-Fe$_3$O$_4$/O$_2$: a green, magnetic, and reusable catalytic system for synthesizing benzimidazoles. J. Chem. 65, 280-285; Safari, J., Sadeghi, M., 2017. Nanostarch: a novel and green catalyst for the synthesis of 2-aminothiazoles. Monatsh Chem. 148, 745-749, each incorporated herein by reference in their entirety]. Preparation of the intermediate given on the proposed mechanism for producing pyrazole derivatives in FIG. 9. Fe$_3$O$_4$NPs as the catalyst can activate the active methylene compounds (A) through coordination with the carbonyl group's oxygen atom. The catalyst can participate in the conversion of (B). Afterward, Fe$_3$O$_4$NPs promoted cyclization with hydrazine hydrate, and dehydration gives pyrazole derivatives (6) as shown in Table 1. The nanocatalyst could be magnetically recovered from the reaction mixture during the work-up procedure. Furthermore, the proposed mechanism for preparing the Schiff base derivatives was carried out by activating aromatic aldehyde by Fe (III) of Fe$_3$O$_4$NPs. Then nucleophilic attack of the amino group to the carbonyl group of the activated aldehyde via the elimination of H$_2$O to give Schiff base derivatives.

Example 8: Biological Activity

All synthesized compounds were tested for their antimicrobial activities against five types of microorganisms, including gram-negative and positive bacteria and fungi. The gram-negative bacteria include *E. coli* and *P. aeruginosa*, while *B. subtilis* and *S. aureus* represented the gram-positive bacteria. *C. albicans* was the fungus used in the screening. Generally, the tested compounds exhibited better antibacterial activities, with *E. coli* being the most sensitive bacteria. However, among all the tested compounds, except compound (7) as shown in Table 2, showed no antifungal activity against *C. albicans*. Azo derivatives (1, 2) and (6-8), were slightly more potent than the Schiff bases, with average zones of inhibition of 15.71 and 12.87 millimeters (mm), respectively. Compound (6) showed the most potent antibacterial activity against *E. coli*, whereas compound (9) was the least potent among the tested series of compounds. Unsubstituted benzene in Schiff base (9) was less potent than the substituted analogs. This may suggest that benzene substitution is beneficial for the activity. In addition, the antibacterial activity of the Schiff bases seems to be insensitive to the position and the nature of the substituents. The majority of the synthesized compounds did not exhibit antipseudomonal activity. Only compounds (6, 9, 11, 13) and (18) showed growth inhibition against *P. aeruginosa*, with the most potent activity observed with compound (6). However, none of the compounds was superior to piperacillin. For the gram-positive bacteria, the antibacterial activity was more significant in Schiff base derivatives when compared to azo derivatives. None of the tested compounds showed superior activity to the positive control. Compound (7) was the only pyrazole derivative that showed activity against both *B. subtilis* and *S. aureus*, whereas compounds (11, 13) and (16) were the only Schiff bases that exhibited activities against both bacteria Table 2.

TABLE 2

Anti-microbial activity of 2-aminothiazoles derivatives (6-18)

| Compound No. | Inhibition Zone(mm ± SD) E. coli | Column 3 P. aeruginosa | Column 4 Bacillus | Column 5 S. aureus | Column 6 Candida |
|---|---|---|---|---|---|
| 1 | 9.8 ± 0.2 | Nil | Nil | Nil | Nil |
| 2 | 10.15 ± 0.4 | Nil | Nil | Nil | Nil |
| 6 | 22 ± 0.8 | 16 | Nil | Nil | Nil |
| 7 | 16 ± 1.4 | Nil | 8.6 ± 0.4 | 12.3 ± 0.9 | 12 ± 0 |
| 8 | 20.6 ± 0.9 | Nil | 10.6 ± 0.4 | Nil | Nil |
| 9 | 8.8 ± 0.4 | 8 ± 0 | Nil | Nil | Nil |
| 10 | 14.3 ± 0.4 | Nil | Nil | Nil | Nil |
| 11 | 12.3 ± 0.9 | 11.8 ± 0.6 | 8.6 ± 0.9 | 10.6 ± 0.4 | Nil |
| 12 | 13.3 ± 1.2 | Nil | Nil | 10.3 ± 0.7 | Nil |
| 13 | 14.95 ± 0.5 | 9 ± 0.8 | 11.3 ± 0.4 | 9.6 ± 0.3 | Nil |
| 14 | 12.3 ± 0.4 | Nil | 10.3 ± 0.4 | Nil | Nil |
| 15 | 12.6 ± 0.5 | Nil | Nil | Nil | Nil |
| 16 | 13 ± 0.4 | Nil | 12.3 ± 0.4 | 13 ± 0.1 | Nil |
| 17 | 10.95 ± 0.3 | Nil | Nil | 9.3 ± 0.4 | Nil |
| 18 | 16.2 ± 0.9 | 14.6 ± 0.7 | 10 ± 0.2 | 11.3 ± 0.4 | Nil |

Concentration of Piperacillin = 4 micrograms per milliliter (μg/ml); Ceftazidime = 1 μg/ml; Oxacillin = 2 μg/ml; Fluconazole = 0.5 milligrams per milliliter (mg/ml)

The present disclosure demonstrates a method for synthesizing pyrazolyl derivatives and 2-aminothiazole Schiff bases derivatives of 2-aminothiazole. This method is efficient and avoids using toxic or heavy metals, high temperatures, with improved product yields, and easy work-up procedure.

Numerous modifications and variations of the present disclosure are possible in light of the above teachings. It is therefore to be understood that within the scope of the appended claims, the invention may be practiced otherwise than as specifically described herein.

The invention claimed is:

1. A method of making a pyrazole compound, comprising:
    mixing a diazonium salt with a reactant in the presence of a solvent thereby coupling a diazo group of the diazonium salt to an α-carbon atom of the reactant to form a reaction intermediate having a formula selected from the group consisting of (I) and (II);
    mixing the reaction intermediate and hydrazine in the presence of a superparamagnetic iron oxide nanoparticles (SPIONs) catalyst thereby cyclizing the hydrazine with an ester group of the reaction intermediate to form the pyrazole compound having a formula selected from the group consisting of (III), and (IV);

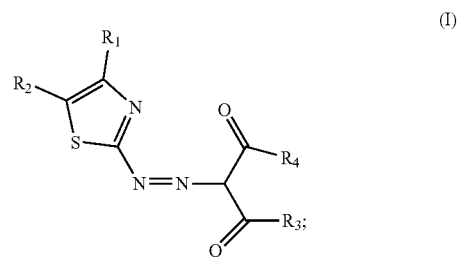

(I)

-continued

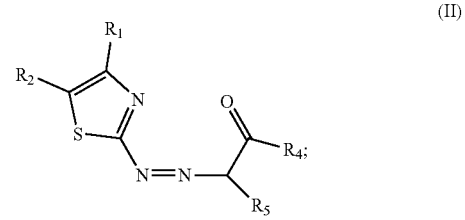

(II)

-continued

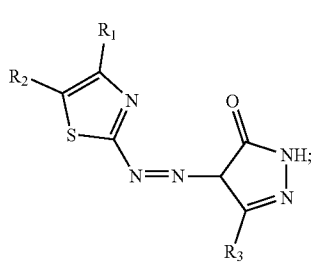

(III)

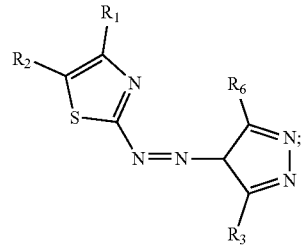

(IV)

and
wherein $R_1$, $R_2$, $R_3$, $R_5$, and $R_6$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group, and wherein $R_4$ is an optionally substituted alkoxy group.

2. The method of claim 1, wherein the reactant has a formula selected from the group consisting of (V) and (VI);

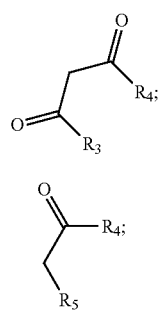

(V)

(VI)

and
wherein $R_3$ and $R_5$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group.

3. The method of claim 1, wherein the reactant is at least one selected from the group consisting of methyl acetoacetate, ethyl acetoacetate, ethyl cyanoacetate, malononitrile and acetylacetone.

4. The method of claim 1, wherein a molar ratio of the diazonium salt to the reactant is in a range of 1:1 to 1:3.

5. The method of claim 1, wherein the solvent is at least one selected from the group consisting of toluene, benzene, dichloromethane, dichloroethane, chloroform, methanol, ethanol, propanol, butanol, dimethylformamide, dimethylacetamide, dimethylsulfoxide, tetrahydrofuran, and acetonitrile.

6. The method of claim 1, wherein the SPIONs catalyst has a formula $Fe_3O_4$, and wherein a molar ratio to the reaction intermediate is in a range of 1:200 to 1:10.

7. The method of claim 1, wherein $R_1$ and $R_2$ are each independently a hydrogen atom, wherein $R_3$ and $R_6$ are each independently selected from the group consisting of a methyl group, and an amine group, and wherein the pyrazole compound is at least one selected from the group consisting of 3-methyl-4-(thiazol-2-yldiazenyl)-1H-pyrazol-5(4H)-one, 3-amino-4-(thiazol-2-yldiazenyl)-1H-pyrazol-5(4H)-one, and (3,5-dimethyl-4H-pyrazol-4-yl)-thiazol-2-yl-diazene.

8. The method of claim 1, wherein the pyrazole compound can inhibit microbial growth of at least one selected from the group consisting of E. coli, P. aeruginosa, B. subtilis, S. aureus, and C. albicans.

9. The method of claim 1, further comprising:
preparing the diazonium salt by:
mixing and dissolving an aminothiazole compound having a formula (VII) in an acid solution to form a mixture;
diazotizing the aminothiazole compound by mixing a nitrite salt with the mixture to form the diazonium salt having a formula (VIII);

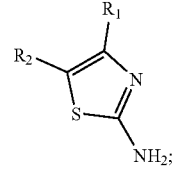

(VII)

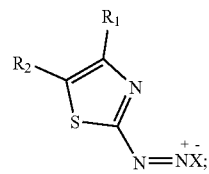

(VIII)

wherein $R_1$ and $R_2$ are each independently selected from the group consisting of a hydrogen atom, an optionally substituted alkyl, an optionally substituted cycloalkyl, an optionally substituted alkoxy, a hydroxyl group, a halogen group, an amine group, a nitro group, and a cyano group; and
wherein X is a halogen atom.

10. The method of claim 9, wherein the aminothiazole compound is present in the mixture at a concentration of 0.1 to 0.6 molar (M), and wherein a molar ratio of the aminothiazole compound to the nitrite salt is in a range of 1:1 to 1:10.

11. The method of claim 9, wherein the aminothiazole compound is 2-aminothiazole, and wherein the nitrite salt is at least one selected from the group consisting of sodium nitrite, potassium nitrite, and lithium nitrite.

12. The method of claim 1, further comprising:
preparing the superparamagnetic iron oxide nanoparticles (SPIONs) catalyst by:
mixing an iron (II) salt and an iron (III) salt in water to form a mixture under an inert atmosphere;
heating the mixture to a temperature of 80 to 100° C., and mixing with an ammonium hydroxide solution to form a reaction mixture having a pH of 8 to 10;

continuously agitating the reaction mixture to form the SPIONs in the form of a precipitate;

removing the precipitate from the reaction mixture, washing, and drying to form the SPIONs catalyst;

wherein the SPIONs are in the shape of spherical particles having an average particle size of 2 to 20 nanometers (nm);

wherein a molar ratio of the iron (II) salt to the iron (III) salt in the mixture is 2:1 to 1:4; and wherein the ammonium hydroxide solution has an ammonia concentration of 15 to 30% by mass.

* * * * *